(12) United States Patent
Strobel et al.

(10) Patent No.: US 6,329,193 B1
(45) Date of Patent: *Dec. 11, 2001

(54) TAXOL PRODUCTION BY A MICROBE

(75) Inventors: Gary Strobel, Bozeman; Andrea A. Stierle; Donald B. Stierle, both of Butte, all of MT (US)

(73) Assignee: The Research and Development Institute at Montana State University, Bozeman, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/047,933

(22) Filed: Mar. 26, 1998

Related U.S. Application Data

(63) Continuation-in-part of application No. 08/258,105, filed on Jun. 10, 1994, now Pat. No. 5,861,302, which is a continuation-in-part of application No. 07/971,508, filed on Nov. 4, 1992, now Pat. No. 5,322,779, which is a continuation-in-part of application No. 07/869,726, filed on Apr. 16, 1992, now abandoned.

(51) Int. Cl.$^7$ ..................................................... C12N 1/14
(52) U.S. Cl. ..................................... 435/254.1; 435/252.1
(58) Field of Search ............................... 435/254.1, 252.1

(56) References Cited

U.S. PATENT DOCUMENTS 5,322,799 * 6/1994 Strobel et al. .
5,861,302 * 1/1999 Stierle et al. .

* cited by examiner

*Primary Examiner*—Leon B. Lankford, Jr.
(74) *Attorney, Agent, or Firm*—McDermott, Will & Emery

(57) ABSTRACT

Taxol is produced from taxol-producing micro-organisms. Methods of obtaining the taxol-producing microorganisms are described. Radioactive labelled taxol products and methods for use of the radioactive labelled taxol and for the treatment of leukemia and cancer cells are described.

8 Claims, 19 Drawing Sheets

1ND 1000x

H10BA2 1000x

WIC65NC 1000x

CC45BD 1000x

CC50NA1 1000x

CC54BE 1000x

CC64BB 1000x

CC54BA 1000x

CC53NA2-1 1000x

CC52NC 1000x

TAXOL PRODUCTION BY A MICROBE

This application claims priority from and is a continuation-in-part of Ser. No. 08/258,105, filed Jun. 10, 1994 now U.S. Pat 5,861,302, which is a continuation in part application of Ser. No. 07/971,508, filed, Nov. 4, 1992, now U.S. Pat. No. 5,322,779, which is a continuation in part of U. S. application Ser. No. 07/869,726, filed Apr. 16, 1992, now abandoned.

TECHNICAL FIELD

The present invention relates to the use of one or more microorganisms to produce taxol (and related taxanes). The invention discloses the method of the discovery of said microorganisms, their isolation, screening for taxol production, growth requirements for taxol production, and chemical evidence for taxol (taxane) production.

BACKGROUND OF THE INVENTION

Taxol, which is of the chemical structural formula:

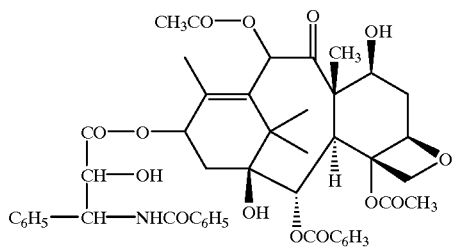

shows significant properties of promoting the polymerization of tubulin and inhibiting the depolymerization of microtubules. For these reasons, taxol is a valuable antileukemic and antitumor agent and is the subject of increasing research.

Taxol is known to be extracted from the trunk bark of different species of the Taxus, or Yew tree. Yields are generally low, usually on the order of no more than about 100 milligrams per kilogram in the extraction process. Various procedures for the production of taxol are known for example, from U.S. Pat. Nos. 4,814,470 and 4,857,653. A chemical process for the preparation of taxol is disclosed in U.S. Pat. No. 4,924,011.

Wani et al, "Journal of the American Chemical Society", Vol. 93, May 1971, No. 9, pages 2325–2327, reports on the structure of taxol and its potential use as an antileukemic and tumor inhibitory compound. This publication further discusses an alcohol extraction procedure for obtaining taxol from the stem bark of the western Yew tree (*Taxus brevifolia*).

The Pacific yew, *Taxus brevifolia*, is one of only ten Taxus species known worldwide. It is not confined to the Pacific coast of North America as its name might imply, but grows inland as far east as Glacier National Park, Montana. Generally, it is a small tree, 7–13 meters in height and 5–10 cm in diameter. The crown is large and conical. Commonly, however, it is contorted with the main stem and some of the lower limbs growing close to the ground producing numerous adventitious roots resulting in a complex and dense interwoven thicket of growth. The tree is usually associated with deep, rich, moist soils near streams and lakes. It is an understory tree commonly found with Douglas fir, Western hemlock, Western red cedar and Western larch.

The inner bark of this remarkable little tree is the primary source of taxol. Taxol is a highly derivatized terpenoid having the structure indicated above, and has shown remarkable promise as an anti-tumor agent especially in breast and ovarian cancers. Unfortunately, at the present time, the supplies of taxol are inadequate to meet the current or projected demands. Taxol is only currently available from extract from the bark of yew trees. The inadequate supply of taxol is reflected in its current market price which is $6000.00 per gram. Thus, it is essential to understand how, where, and when, taxol is biosynthesized in the tree and the factors that affect its biosynthesis.

It is likely that many factors influence the production of taxol by Pacific yew. These include not only various environmental factors such as temperature and moisture level, but the genetic background of the tree itself. Also, plants are commonly hosts to a multitude of microbes including parasites, symbionts, endophytes, epiphytes, and mycorrhizal fungi. These organisms may also influence the production of secondary plant metabolites such as phytoalexins, whose presence can be triggered by elicitors from microbes. Such microbes may catabolize or derivatize plant compounds.

These and other reasons prompted the present inventors to devise an "sin vitro" system of taxol production (see related U.S. patent application Ser. No. 07/845,097, filed Mar. 3, 1992, now U.S. Pat. No. 5,456,392. The system utilizes isotopic precursors of taxol, an optimized environment and the appropriate plant parts where taxol is synthesized. The result was an "in vitro" system of taxol synthesis from the most productive tissue portions of the Pacific yew tree.

However, the above in vitro synthesis described in U.S. Pat. No. 5,456,392 has certain limitations. The source of taxol production, the Pacific yew, is a relatively rare tree, and there is concern that the supply of taxol is not adequate to meet the demand.

Moreover, other methods, including total chemical synthesis, and derivatization of baccatin to yield taxotere are both inadequate. The chemical synthesis methods are multi-stepped and non-economically feasible while the taxane derivatization method utilizes a taxane isolated from yew needles.

Clearly, a microbial source of taxol would be preferable if it could be easily grown, would produce taxol (or a related taxane), and utilize the enormous U. S. biotechnology industry fermentation capabilities.

SUMMARY OF THE INVENTION

Accordingly, it is an object of the present invention to provide an improved process for producing taxol, using a taxol producing microbe followed by separation of taxol from the growth medium and/or microbe. The invention is considered to be broadly directed to any microbe which will produce taxol, regardless of source.

In a further embodiment of the invention, there is provided a radioactive labelled taxol product and methods for use of the radioactive labelled taxol. The labelled taxol can be produced by use of a labelled precursor as described herein. Radiolabelled taxol is a new compound for the present invention and related U.S. Pat. No. 5,456,392 (which produces the labelled taxol by a different process). Because of its radiolabel, it and its derivatives can be identified in the mammal body so one can determine how it functions as an antileukemic and antitumor agent. The taxol may be labelled with any label (stable or unstable) including $^{14}C$, $^{13}C$, tritium ($^{3}H$) or with $^{15}N$.

STATEMENT OF THE INVENTION

The present invention provides an improved process for producing taxol, which uses a taxol producing microorganism followed by separation of taxol from the growth medium and/or microorganism. One aspect of the invention is a method for isolating a microorganism which produces a taxane, which comprises the following steps:

(a) obtaining tissue fragments from a source such as a tree of the Genus Taxus, or other material which is a source of taxol, (b) placing said tissue fragments on agar medium until fungal growth occurs e.g., about 2–5 days, (c) placing fungal hyphae from said fungal growth on mycological agar, and replacing said fungal hyphae on said mycological agar if necessary, until a culture in pure form is obtained, (d) transferring said fungal hyphae to a fungal lab growth medium, with subsequent growth of the fungal culture, (e) removing at least a portion of the culture media containing the fungal culture, thoroughly grinding the mycelium, and adding an organic solvent to the mixture, (f) obtaining a chromatograph of said fungal culture in said solvent, (g) checking the solution for the taxane reaction, e.g., with vanillin-sulfuric acid spray, and comparing the chromatograph with one or more taxane standards such as taxol, baccatin, cephalomannine, and optionally (h) discarding the cultures which do not produce taxol. Optionally, the cultures which do not produce taxol may be preserved for additional testing.

Preferred members of the Genus Taxus are *Taxus brevifolia, Taxus baccata, Taxus cuspiduta, Taxus canadensis,* and *Taxus floridana.* Particularly preferred is *Taxus brevifolia.*

The present invention further provides a class of microbes such as fungi and bacteria, which have taxol-producing characteristics. Montana BA, the characteristics of which are described in detail below, is representative of such microbes. Multiple additional taxol producing microbes are also disclosed. The microbes according to the present invention produce taxol in culture. Preferred taxol-producing microbes are fungi, and particularly preferred is a taxol producing fungi isolated from trees such as yew trees and others as described below. Even more preferred is a fungus designated Montana BA. The present invention provides the major discovery of microbes which will produce taxol. The invention covers any microbe which has taxol producing characteristics. The specific microbes described are considered representative only and other microbes may be obtained from any source.

Also, the present invention comprises a taxane composition obtained by culturing a microbe. Preferred is a taxane of the species taxol. Particularly preferred is a taxol composition produced by a microbe, e.g., a fungus having the taxol-producing characteristics of Montana BA.

In another aspect, the present invention provides a radiolabelled taxane composition obtained by culturing a microbe. Preferred is a radiolabelled taxol composition produced by a microbe which is a fungus. Even more preferred is a labelled composition produced by a microbe which is a fungus having the characteristics of Montana BA. Particularly preferred labels are $^{14}C$, $^{13}C$, $^{3}H$, or $^{15}N$.

The present invention provides an improved method for producing a bulk pharmaceutical composition, which contains a pharmaceutically effective amount of a taxol composition, combined with one or more pharmaceutically acceptable inert or physiologically active diluents or adjuvants.

Also provided is a pharmaceutical composition, which contains a pharmaceutically effective amount of a radiolabelled taxol composition, as described above, combined with one or more pharmaceutically acceptable inert or physiologically active diluents or adjuvants.

Moreover, the present invention includes a method for the treatment of leukemia or tumors which comprises administering a pharmaceutical composition containing taxol as described above.

In yet another aspect, the present invention provides a method for producing a taxane, which comprises a) exposing a taxane producing microbe according to the present invention as described above to a nutrient media capable of supporting growth of the microbe, b) providing culturing conditions for the media containing the microbe, which conditions are capable of producing growth and reproduction of the microbe, and c) isolating or concentrating the desired taxane from said culture media or said microbe.

Preferred is a method for producing a taxol composition wherein the microbe has the taxol-producing characteristics of Montana BA. More preferred is such a method wherein the microbe is a taxol producing fungi. Further preferred is a method wherein the microbe is isolated from a yew tree, any other tree, or any other source of taxol microbe.

Also preferred is a method for producing a taxane, as described above, wherein the nutrient media comprises benzoic acid, a benzoic acid metabolite precursor, or a salt of benzoic acid, such as sodium benzoate. Particularly preferred is a method as described above for producing the taxane, wherein the taxane is taxol.

A preferred method for producing a taxane comprises a) exposing a taxol producing microbe to a nutrient media capable of supporting growth of said microbe, b) providing culturing conditions for said media containing said microbe, which are capable of producing growth and reproduction of said microbe, and c) isolating or concentrating said taxane from said culture media or said microbe.

Also preferred is a method for producing a taxane which comprises a) exposing a taxol producing microbe of the invention to a nutrient media capable of supporting growth of said microbe, wherein said media contains benzoic acid, b) providing culturing conditions for said media containing said microbe, which conditions are capable of producing growth and reproduction of said microbe, and c) isolating or concentrating said taxane from said culture media or said microbe.

In another preferred aspect of the present invention provides a method for producing a taxol which comprises a) exposing a taxol producing microbe of the invention to a nutrient media capable of supporting growth of said microbe, wherein said media contains benzoic acid, b) providing culturing conditions for said media containing said microbe, which conditions are capable of producing growth and reproduction of said microbe, and c) isolating or concentrating said taxol from said culture media or said microbe.

DESCRIPTION OF THE INVENTION

Figure 1:
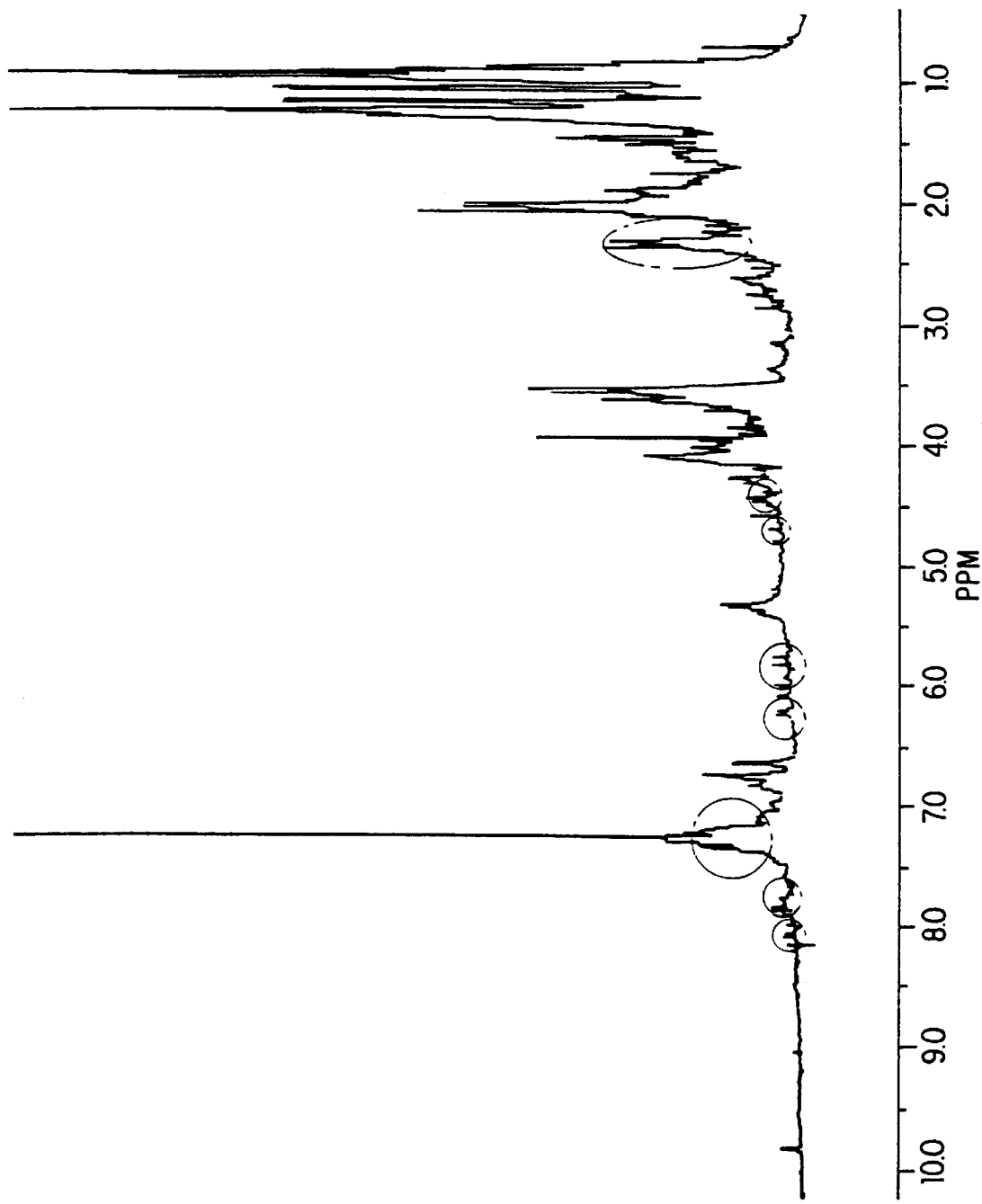
FIG. 1 shows the NMR spectrum of a semi-purified culture extract from Montana BA fungus.

All land plants serve as life support systems to a host of microbes. The microbes exist as parasites, saprophytes, endophytes, symbionts or mycorrhizae. On occasion, there may be intergeneric exchange of genetic information between one or more of these organisms and its hosts, or vise versa. With the former case, it is well documented that certain species of agrobacteria are capable of genetically transforming their host plants via either the Ri or Ti plasmids. The result is that a genetically altered plant is formed that has one or more characteristics of the agrobacterium.

Numerous cases are known in which all phytohormones, known throughout the plant kingdom, are also produced by one or more plant parasitic bacteria or fungi. These include indole acetic acid, the gibberillins, some cytokinins, abscissic acid and ethylene. Recently, the present applicants have also shown that certain terpenoids that were originally thought to be exclusively higher plant associated compounds, are also produced by a plant pathogenic fungus (See, Bunkers et al., "Production of Petasol", Mycol. Res 95, (3); 347–351 (1991)).

Thus, while there is no published evidence that taxol could or would be produced by any microorganism, the present applicants explored the microorganism possibility. The inventors suspected that taxol (taxanes) may be produced by one or more microbes associated with various trees, especially the yew tree, and other species of trees as described herein, and especially in fungi found in trees.

The basis for this concept was that microbes may exist which will produce taxol because of a possible genetic exchange which may have previously occurred, either between the microbe(s) (as original source of taxol) or a tree such as a yew tree (as original source of taxol). The net result would be the most desirable case of possessing one or more microbes which could be placed in fermenters to produce taxol.

The present invention provides a method for locating and isolating microorganisms which produce taxol, and provides specific examples where such taxol producing organisms are found. Other microorganisms associated with the yew or related trees, which produce taxol or related taxanes, may be isolated using the present method. Therefore, the present invention is considered to be inclusive of all such microbes.

One method of the invention involves finding, isolating and characterizing one or more microbes from forests or isolated stands of yew or other trees or elsewhere, which produce taxol (taxanes). One place to focus the search for such an organism was in one or more locations which have naturally supported the growth of source trees for centuries.

After locating the yew or other tree, the following general method is followed to isolate microbes which produce taxol.

Small stems were cut from the yew tree, treated with 70% ethanol as a disinfectant and then, with a sterile blade, removing the outer bark. Pieces of the inner bark of the stem, which is enriched with taxol (Wani's paper), are then placed on agar medium (water agar) until fungal growth occurs after 2–5 days. Then, tips of the fungal hyphae are removed from the water agar and subsequently placed on mycological agar. The culture is obtained in a pure form as judged by its behavior on the plate. Lab contaminants seldom occur due to the rigor of the aseptic technique which was used.

Once the organism is obtained in a pure form it is ultimately transferred to one or more lab media. In this case the modified M-1-D medium (Table 1, below) with yeast extract is used to support the growth of the microbe. Alternatively, (Table 2, below) another medium which resembles the soluble sugars (quantity and quality) of the yew bark, plus a mixture of amino acids (or critical amino acids and another nitrogen source, such as ammonium salts), Na benzoate and acetate are included.

TABLE 1

Modified M-I-D Media (Filner)

|  |  | g/l |
| --- | --- | --- |
| Ca (NO$_3$)$_2$ | 1.20 mM | 0.28 |
| KNO$_3$ | 0.79 mM | 0.08 |
| KCl | 0.87 mM | 0.06 |
| MgSO$_4$ | 3.00 mM | 0.36 |
| NaH$_2$PO$_4$-H$_2$O | 0.14 mM | 0.02 |
| Sucrose | 87.60 mM | 30.00 |
| Ammonium Tartrate | 27.10 mM | 5.00 |
|  |  | mg/l |

TABLE 1-continued

Modified M-I-D Media (Filner)

| | | |
|---|---|---|
| FeCl$_3$-6H$_2$O | 7.4 µM | 2.0 |
| MnSO$_4$ | 30.0 µM | 5.0 |
| ZnSO$_4$-7H$_2$O | 8.7 µM | 2.5 |
| H$_3$BO$_3$ | 2.2 µM | 1.4 |
| KI | | 4.5 µM 0.7 | pH 5.5 with 0.1M HCl
0.25 g Yeast Extract*
*Or omit the Yeast and supplement with:
Stock Biotin 0.5 mg/ml
Stock Thiamine 0.5 mg/ml in 40% aq. EtoH
Stock Inositol 5 mg/ml
Use 2 ml/l of broth

TABLE 2

Taxol Microbial Culture Medium

| | Grams/Liter |
|---|---|
| glucose | 1 |
| fructose | 3 |
| sucrose | 6 |
| KHPO$_4$-KH$_2$PO$_4$ | 1 ml of 1M pH 6.8 |
| MgSO$_4$ | .36 |
| Ca(NO$_3$)$_2$H$_2$O | .65 |
| Yeast extract | 0.5 g |
| Ca(NO$_3$)$_2$ | 1.0 mg |
| ZnSO$_4$ | 2.5 |
| MnCl$_2$ | .5 |
| FeCl$_2$ | 2.0 |
| leucine | 0.1 mM |
| phenylalanine | 0.01 mM |
| NaAc | 1.0 mM |

The incubation of the fungus is carried out at 2° C. (in 100 ml of medium in a 250 ml flask, for example) under still conditions (occasionally shake periodically—every other day, for example) for 3 weeks. At the end of the incubation period the fluid (media) is decanted and the mycelium is thoroughly ground (disrupted) at maximum speed in a Sorvall Ominimixer for 30 sec. Then, an equal volume of chloroform methanol solution 10:1 v/v is added to the medium and ground fungal mycelial solutions. The chloroform layer (bottom) is removed in a separatory funnel. The process may be twice repeated. Ultimately, the chloroform layers are collected together and subjected to flash evaporation under a vacuum at 35–40° C. until dry.

A portion of the residue is then chromatographed on a 5×10 cm plate of silica gel in solvent B (below) (Merck silica gel 0.25 mm). Authentic standards of taxol, baccatin, and cephalomannine are also chromatographed for comparison.

The aqueous layer is lyophilized and thoroughly extracted with chloroform methanol 1:1. When evaporated, it is chromatographed in the same manner as above.

The standard solvents used in the chromatographic procedures are:

A) chloroform/methanol 7:1 V/V
B) chloroform/acetonitrile 7:3 V/V
C) ethyl acetate/isopropanol 95:5 V/V
D) methylene dichloride/tetrahydrofuran 6:2 V/V.

The taxanes (taxol, baccatin, cephalomannine) all absorb short wave UV light (254 angstroms) and react with the vanillin-sulfuric acid spray (see, Cardellina, J. Liquid Chromatography 14: p 6659–665 (1991) to produce an intense blue coloration fading to gray then turning brown after 24 hours. Each fungus culture was treated in the same manner.

At least 50 fungi and 10 bacteria were isolated from yew roots, needles, stems, or fruits and tested. Samples of the extract from each organism were subjected to initial screening by thin layer chromatography (TLC) in solvent A.

A few microbes appeared promising after the initial screening. That is, their extract produced a blue spot at R$_f$ 0.75–0.81 in solvent A (same as taxol). These microbes were fungi and one later identified as *Cladosporium macrocarpum*, was further checked for taxol by other methods—but without success. A strain of fungus, designated Montana BA, exhibited several important absorbances in HNMR consistent with the spectrum of taxol (see FIG. 1). Therefore, this culture held promise for taxol production and was studied further. The following are descriptions of the fungus and taxane production.

(1) Montana BA—rapidly growing on potato dextrose agar, most hyphae with growth oppressed to agar surface, no apparent fruiting structures, beige coloration of hyphae. (Culture on deposit with the Central Bureau voor Schimmelcultures under the terms of the Budapest Treaty as Accession No. CBS 279.92).

(2) Evidence for taxol (taxane) production (a) The fungus was grown in both M-1-D and Taxol Microbial culture medium (2 liters) for 3 weeks at 25° C. with only periodic shaking. The medium and the grown mycelium were extracted with chloroform:MeOH 10:1 v/v.

After evaporation of the chloroform:MeOH the residue was taken up in 0.5ml of CHCl$_3$ MeOH 10:1 v/v and subjected to preparative TLC in solvent B on Merck plates 0.5mm (20×20). A band at R$_F$ 0.47–0.50 that had slight UV (254 angstroms) absorbance and gave a slight reaction with the vanillin sulfuric acid spray was scraped from the plate and eluted with acetonitrile. Only the extreme edge is sprayed, unadulterated material is scraped and eluted.

Figure 2:
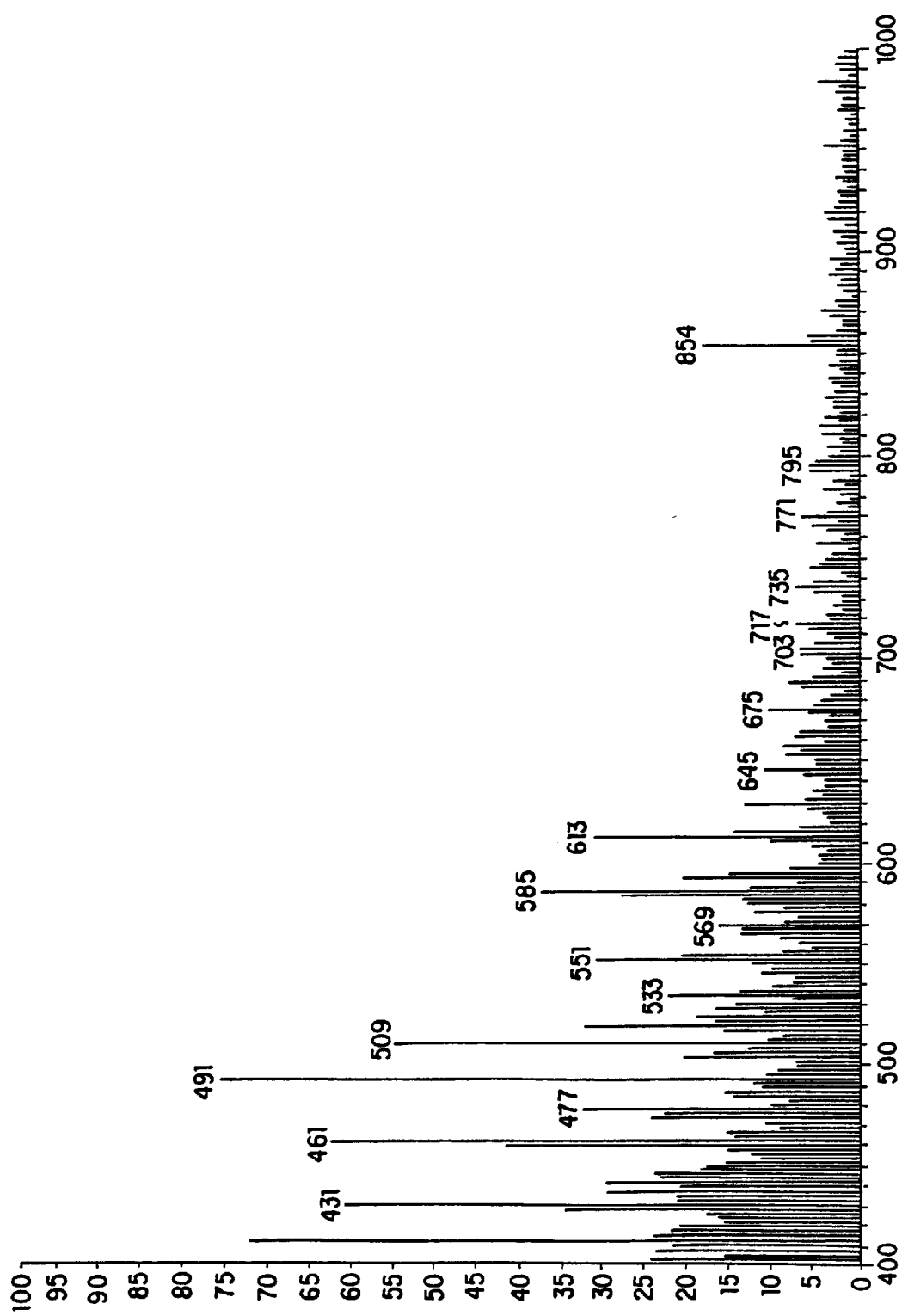
FIG. 2 shows a FAB mass spectrum of taxol obtained by culturing the Montana BA fungus.

Further chromatography was done in solvent A in TLC (precleaned plates with the same solvent). The "taxol" band was eluted and subjected to spectroscopy. This band had the same FAB mass spectrum as authentic taxol with an M$^{+1}$ at 854 and prominent peaks at 491, 509 and 613 (see FIG. 2).

The UV spectrum of the compound had an absorption maximum at 273 nm which is identical to authentic taxol (see Wani et al). The NMR spectrum of the semi-purified compound possessed all of the major absorbances of authentic taxol (FIG. 1).

In addition, the R$_F$ values for the taxol preparation from the fungus "Montana BA" was identical to authentic taxol (see Table 3 below).

TABLE 3

Comparative R$_F$ values of fungal taxol to authentic taxol and baccatin

| Solvent System: | |
|---|---|
| CHCl$_3$/MeOH 78:1 v/v | |
| taxol | .81 |
| fungal | .81 |
| baccatin | .75 |
| fungal baccatin | .75 |
| CHCl$_3$ Acetonitrile 7:3 v/v | |
| taxol | .47 |
| fungal taxol | .47 |
| baccatin | .50 |
| fungal baccatin | .50 |

TABLE 3-continued

Comparative $R_F$ values of fungal taxol to authentic taxol and baccatin

Solvent System:

Ethyl acetate isopropanol 95:5 v/v

| | |
|---|---|
| taxol | .63 |
| fungal taxol | .63 |
| baccatin | .58 |
| fungal baccatin | .58 |

$Ch_2Cl_2$ Tetrahydrofuran 6:2 v/v

| | |
|---|---|
| taxol | .75 |
| fungal taxol | .75 |
| baccatin | .67 |
| fungal baccatin | .67 |

It is also to be noted that the compound "baccatin", a taxane related to taxol, also appeared in the fungal extract. It, along with taxol, yielded the same intense blue color reaction and the same UV (254) absorption properties as the authentic compounds. It also had the same $R_F$s as authentic baccatin (Table 3).

TABLE 4

Enhanced Taxol Microbial Culture Medium

| | Grams/Liter |
|---|---|
| glucose | 1 |
| fructose | 3 |
| sucrose | 6 |
| $KHPO_4$-$KH_2PO_4$ | 1 ml of 1M pH 6.8 |
| $MgSO_4$ | .36 |
| $Ca(NO_3)_2H_2O$ | .65 |
| Yeast extract | 0.5 |
| $Ca(NO_3)_2$ | 1.0 mg |
| $ZnSO_4$ | 2.5 |
| $MnCl_2$ | 0.5 |
| $FeCl_2$ | 2.0 |
| phenylalanine | 5.0 mg |
| NaAc | 1.0 g |
| Sodium Benzoate | 10 mg–100 mg |

The amount of taxol per liter (3 wk old culture) is estimated at about 1–2 µg. Baccatin appears at a level of 0.5–1 µg/liter.

The taxonomy and properties of the microbe revealed a fungus of the family *Fungi imperfecti* (or alternatively called the family Hyphomyces). The genus was determined to be *Taxomyces* and the species was named andreanae.

*T. andreanae* (Montana BA) forms the bulbil or sterile cell masses which appear to be unique structures.

Type species: *Taxomyces andreanae* Strobel, Stierle, & Hess. 30 Holotypus: Based on material taken from the bark of *Taxus brevifolia* Nutt. infested living bark samples, agar slants containing the type are deposited with the Montana State University (MSU) mycological collection, D. E. Mathre, Department of Plant Pathology, Montana State University—col. no. 738. Duplicate cultures are deposited at the CBS, Baarn, Holland 25 culture 279.92.

A pure culture species was obtained of Montana BA which was named *Taxomyces andreanae* S1. Two further fungal cultures, other than Montana BA, which produced taxanes were obtained from the above screening. Their characteristics revealed them to be of the same genus and species, but to have slightly different properties in that each strain differed in hyphal morphology and growth. These microbes were isolated to pure culture form and given the names *Taxomyces andreanae* 52 and *Taxomyces andreanae* 53, respectively. Further details are presented below in the experimental section.

(b) To dispel the notion that the taxol isolated from the culture medium might be occurring as a result of the fungus's previous association with the yew tree, the fungus "plugs" used to inoculate the medium were exhaustively extracted and the residue chromatographed. There was no evidence of taxol.

(c) In order to be assured that taxol is produced "de novo" by the fungus, the fungus was incubated for 3 weeks in two 500 ml cultures of Taxol Microbial Culture medium and added 100 µCi of NaAC-1-$^{14}$C (54mCi/mole) plus 125 µCi of mixed amino acids 1.75mCi/mg. Both the taxol and baccatin areas on the preparative TLC's were isolated and then subjected on 2 plates to 3 dimensional TLC (20×20 plate—25 mm layer) along with (co-chromatography) authentic taxol and baccatin. The UV absorbing spot was removed by scraping and counted by liquid scintillation counting methods. The results show that the area on the plates having radioactivity was identical to the UV absorbing spot. This was true on both taxol and baccatin. This test assures that both baccatin and taxol were synthesized 'de novo' by the fungus.

Throughout the course of the taxol microbial study, a means of determining the cytotoxicity of the culture extracts and various column fractions to facilitate bioassay guided fractionation was needed. Ferrigni et al., J. Nat. Prod. 45, 679 (1982); and Ferrigni et al., J. Nat. Prod. 47, 347 (1984), suggested that a simple brine shrimp assay provided a reasonable facsimile of the standard anticancer assays. Those authors were able to isolate the antileukemic principles from the seeds of *Euphorbia lagascae* Spreng using a fractionation scheme guided by brine shrimp and potato disc assays. Several studies have demonstrated good correlation between brine shrimp lethality and cytotoxicity.

The brine shrimp bioassay is a simple test. Brine shrimp are hatched in Instant Ocean dissolved in tap water, which generates a solution that approximates the constituents of sea water. The test material is handled according to its polarity and purity. Crude culture residues are tested at 10 mg, simply dissolved in the saline water used to rear the brine shrimp. The test material is dissolved in 2 ml of salt water, and an additional 2 ml of salt water containing the brine shrimp is added. The brine shrimp are counted, then recounted at various time intervals. Toxicity is determined by the number of brine shrimp deaths which result from the test material, relative to a control of saline water, and a control of authentic taxol.

Biological activity of the Montana BA extract showed positive α-action (antitubulin) activity which is the comparable activity observed for authenane producing characteristics, especially as described in the present invention, irrespective of their source. Such microbes are those which can produce taxol by the NMR spectrum of FIG. 1, the FAB mass spectrum of FIG. 2, the SEMS of FIGS. 4, 5 and 6 and the TEM of FIGS. 8 and 9.

Other than the yew tree, taxol producing microbes have also been obtained according to this invention from *Torreya Grandifolia, Tsuga Canadensis,* Covylus (Filbert), Bristle Cone Pine, White Bark Pine, Torreya Taxifolia, Canadian Hemlock, Western Red Cedar, Cypress, Cephalotaxus, and Wollemi Pine Trees. As described herein, using the methods of the invention, taxol producing microbes, and especially fungi producing microbes, are available from a wide assortment of trees and other sources. Accordingly, this invention is not to be considered as limited to any particular source of microbe. Applicants' invention primarily resides in the discovery that microbes, especially fungi and bacteria, can serve as a source of taxol.

In another aspect of the invention, referred to above, an appropriately labelled precursor is used to produce labelled taxol. $^{14}$C-phenylalanine is the preferred amino acid precursor, for $^{14}$C-taxol production. However, as in the above example, Na acetate-1-$^{14}$C can be used because of its relatively low price and ability to label taxol uniformly.

The taxanes, e.g., taxol, or radiolabelled taxanes produced according to the present invention, can also be provided as a pharmaceutical composition in combination with one or more pharmaceutically acceptable inert or physiologically active diluents or adjuvants. These compositions may be prepared in any form appropriate for the administration route desired. The parenteral route and especially the intravenous route are preferred methods of administration. Compositions for parenteral administration may be aqueous or nonaqueous sterile solutions, suspension or emulsions. Propylene glycol, vegetable oils, injectable organic esters and the like, may be used as solvents or vehicles. The compositions may also contain adjuvants, wetting agents, emulsifiers or dispersants. The compositions may also be in the form of sterile solid solutions which may be dissolved or dispersed in sterile water or any injectable sterile medium. The pharmaceutical compositions may be particularly used in the treatment of acute leukemia and solid tumors at doses known to the art, but generally in the range of between one and two milligrams per kilogram of body weight by the intravenous route for an adult. The pharmaceutical compositions should contain about 0.001 to 1.0 wt. % of effective ingredient and administered in dosage amounts known to the art for taxol.

The above microbial culture method allows for bulk compositions comprising amounts of taxanes, i.e., taxol, in bulk quantities not previously available. Previously, only small amounts of taxol, e.g., only a few hundred milligrams, have been available from extraction and other methods.

An especially important aspect of this invention resides in the discovery that numerous fungi and bacteria, obtained from any source, can produce taxol or taxol containing substances. Fungi are especially preferred as the microbe especially fungi such as *Fungi Imperfecti,* Taxomyces, Pestalotia, Pestalotiopsis, Perconia sp, Alternaria, Trichoderma, Trichosporiella, Monochaeta, Cephalosporim/Acremonium, Fusarium, Coniothyrium, Curvularia, Pennicillium, Ni (Pycnidia), *P. quelpii,* and Xylaria. As can be understood, taxol-producing microbes are found in a wide variety of fungi.

Periconia sp. was isolated from *Torreya grandifolia* (a relative of yew not containing taxol) near Huangshan National Park in the People's Republic of China. This fungus, not previously commonly known as a tree endophyte, was isolated from the inner bark of a small lower limb. In a semi-synthetic medium, Periconia sp., produced detectable quantities of the anticancer drug taxol. Other taxol producing endophytes were also isolated from this source. The presence of taxol was demonstrated unequivocally via spectroscopic and immunological methods. However, successive transfers of the fungus in two semi-synthetic media resulted in their gradual attenuation until little or no taxol production occurred even though fungal growth was relatively unaffected. Several compounds, known previously as activators of microbial metabolism, including serinol, p-hydroxybenzoic acid, and a mixture of phenolic acids, were capable of fully or partially restoring taxol production to otherwise taxol-attenuated cultures. However, the compound with the most impressive ability to activate taxol production was benzoic acid at 0.01 mm. As pointed out above, taxol is a complex diterpenoid produced by all species of taxus (yew). This compound is a potent antifungal agent and probably serves the tree by protecting it against the effects of potential pathogens, especially the water molds (oomcetes). The mode of action of taxol on the oomycetes appears to be identical to its activity against a number of human cancer cells by preventing the depolymerization of tubulin during cell division.

Since the amount of taxol found in the yew trees is relatively small, c.a. 0.01–0.03% dry weight, this has been the major factor contributing to the high price of this drug. With the discovery that certain endophytic fungi are able to produce taxol has come the possibility that a cheaper and more widely available product may eventually be available via industrial fermentation. This invention is based on the discovery that fungi, representing such genera as Taxomyces, Pestalotiopsis, Monochaetia and Alternaria, and others, will produce taxol under standard conditions of fermentation. This invention also demonstrates taxol production by a novel endophytic fungus of trees, Periconia sp., and also shows that taxol production seems to be inducible in this fungus. The fungus used in this work was one of many recovered from a 1.0 cm (dia×3.0 cm (length) limb removed from a 15–20 m high *Torreya grandifolia* tree growing between Huangshan City and Huangshan Park in S.E. mainland China (P.R.C.). The stem was surface treated with 70% ethanol (v/v), the outer bark removed with a sterilized sharp blade, and the inner/phloemcambium tissue pieces placed on water agar in Petri plates. After several days individual hyphal tips of the fungal colonies were moved and placed on potato dextrose agar (PDA), incubated for 8–10 days, and periodically checked for culture purity. Eventually, each pure culture was transferred again, by hyphal tipping, to a Petri plate containing water agar and small pieces of sterilized carnation leaves. The gamma-irradiated leaves commonly encourage the development of fungal fruiting structures which aid in their identification. The fungal isolates, obtained from *T. grandifolia,* were numbered and stored in distilled $H_2O$ at 4° C. as agar plugs and in 15% (v/v) glycerol at −70° C. as spores and mycelium.

Fungal Identification by Microscopy

Fungal spores and fruiting bodies appearing on the carnation leaf fragments were examined by stereo and light microscopy for measurement and identification. Reference strains from the Centraalbureau voor Sch8immelcultures (CBS), Baarn, The Netherlands, were used for comparison. Comparisons of the culture characteristics were made by standard methods after growing the organism on PDA at 23° C. Fruiting structures were fixed and processed using the methods of Upadhyay et al. *Mycol. Res.* 94: 785–791, except that they were placed in 2% (v/v) glutaraldehyde in 0.1 M sodium cacodylate buffer (pH 7.2). The samples were critical point dried, gold coated with a sputter coater and observed and photographed with a JEOL 6100 scanning electron microscope.

Fungal Culturing and Taxol Isolation

The fungi were grown in 2 liter Erlenmeyer flasks containing 500 ml MID medium supplemented with 1 g soytone $1^{-1}$. After 3 weeks of still culture at 23° C., the culture fluid was passed through four layers of cheesecloth to remove solids. After methylene chloride extraction, the extract of each fungal isolate was examined for the presence of taxol by immunological method.

All comparative thin layer chromatography (TLC) analyses were carried out on Merck 0.25 mm silica gel plates developed in the following solvents: A, chloroform/methanol (7:1, v/v); B, chloroform/acetonitrile (7:3, v/v); C, ethyl acetate/2-propanol (95:5, v/v); D, methylene chloride/tetrahydrofan (6:2, v/v); and E, methylene chloride/methanol/dimethylforamide (90:9:1, by vol.). Taxol was detected using a spray reagent consisting of 1% vanillin (w/v) in sulfurinc acid after gentle heating. It appears as a bluish spot fading to dark grey after 24h.

Spectroscopic Analyses

After isolation from fungal cultures, the putative taxol was dissolved in 100% methanol and examined with a Beckman D-50 spectrophotometer. Electrospray mass spectroscopy was done on samples dissolved in methanol/$H_2O$/acetate acid (50:50:1, by vol.) It was injected with a spray flow of 2 $\mu$l min$^{-1}$ with a spray voltage of 2.2 kV by the loop injection method. Nuclear magnetic resonance spectroscopy (NMR) was done on taxol preparations in a Brucker 500 MHz instrument with the sample dissolved in 100% deuterated methanol. The sample was subjected to 2048 scans with a sweep width of 6024 and 8K real points.

Taxol Immunoassays and Quantitation

Fungal extracts were dissolved in methanol at 50 mg$^{-1}$. The insoluble materials were removed by centrifugation in a microfuge for 10 min. Taxol in samples was assayed by competitive inhibition enzyme immunoassay (CIEIA) method Grostams et al., *J. Immunol. Meth.*, 158:5–15. The assay was carried out using a taxol immunoassay kit (Hawaii Biotechnology Group) according to the procedure recommended by the suppliers. In brief, this assay was performed in a 96-well microtitre plate coated with taxol-protein coating antigen. The plate was blocked with 1% (w/v) BSA in PBS. After washing, the solid-phase-bound taxol and was incubated with samples and taxol standards and a specific monoclonal antibody. The taxol in the sample competes with solid-phase-bound taxol was detected by an alkaline-phosphatase-conjugated second antibody and alkaline phosphatase substrate, p-nitrophenol phosphate. The inhibition of color development was proportional to the concentration of free taxol present in samples. The amount of taxol in each sample was calculated from an inhibition curve made by using different concentrations of standard taxol supplied with the kit. This technique was used to screen for taxol in each of the fungal extracts. The assay is sensitive to about 1 ng ml$^{-1}$.

Plant Extracts

Aqueous extracts of several tree species were made by soaking 20g of chopped leaf and stem fragments in 1 l of Hsp for 3 days at 20° C. The sample was filtered through 4 layers of cheesecloth and taken to dryness by flash evaporation at 40° C. Ultimately, each sample was taken up in a small volume of $H_2O$ and then lyophilized to produce a whitish powder. However, some samples were further separated into cation, anion, neutral and lipid fractions. Initially, the aqueous extract was treated with 3 individualized equal volumes of $CH_2Cl_2$ and this solvent, after separation, was taken to dryness by flash evaporation and considered as the "lipid faction". The remaining aqueous sample was separated by sequential passages over 3×6 columns of Dowex 50 H, and Dowex 1-formate. Elution of the Dowex 50 was done with 6N TFA yielding the "cation faction", while Dowex 1 was eluted with 6N formic acid yielding the "anion faction". The neutral faction freely passed through both columns.

Torreya and Taxus are the only two genera in the family taxaceae. Although all Tax spp. produce taxol, little or no taxol is detectable in representative species of Torreya. Torreya and Taxus generally share relatively the same type of habitats, that is moist hillsides or valleys at 1000–3000 m in elevation. In Mainland China, several species of Torreya are found and they are so common that they are harvested for timber and fuel. Since several fungi have been found as endophytes of Taxus sp. it was of interest to learn if Torreya sp. supported taxol-producing endophytic fungi.

From one limb piece of *T. grandifolia* that was sampled, 25 endophytic fungi were recovered. The most frequently recovered endophytic genus was Pestalotiopsis spp. (7/25) with one of these being a taxol producer. Others found were Phoma sp., Fusarium sp., Acremonium sp., Nigrospora sp., and several sterile fungi (producing no fruiting structures) none of which produced taxol. However, at least four other sterile fungi were modest taxol producers. Of the fungi isolated, the most interesting was Periconia sp. since it is not commonly known as an endophytic fungus associated with tree species. Its identity was confirmed by Dr. W. Grams of the CBS, Baarn, The Netherlands On PDA, it characteristically produced on conidiospores in long chains. However, on the carnation leaves in water agar individual conidiospores are dark, long, stout, and shortly branched near the apex bearing one or more loosely connected group of conidia. The individual conidia are highly decorated having protrusions and commonly bearing a tubular segment of the conidiospore if they were borne on PDA.

Taxol from Periconia sp.

A compound having chromatographic properties identical to authentic taxol in solvent systems A-E, a giving a blue-grey color reaction with the vanillin/sulfuric acid reagent was consistently isolated from Periconia sp. Uninoculated culture media did not have such a compound. Furthermore, the compound isolated from this fungus yielded a UV absorption spectrum that was identical to authentic taxol. In addition, the fungal compound produced an NMR spectrum identical to that of authentic taxol. Further convincing evidence for the identity of the compound as taxol was obtained by electrospray mass spectroscopy. Characteristically, authentic taxol yields both an (M+H) peak at 854 and (M+Na)$^+$peak at 876. The product of Periconia sp. produced a spectrum identical to authentic taxol Periconia sp. typically produced 300–400 ng taxol/l as estimated by the immunoassay procedure. This is 6–8 times greater than the yields of taxol originally observed being produced by *Taxomyces andreanae* and about 100 times less than *P. microspora*.

Attenuation of Taxol Production

When the original culture (directly isolated from *T. grandifolia*) of Periconia sp. was grown from 3 weeks on the MID medium supplemented with 1 g/l of soytone solvent ca. 350 ng taxol/l was produced. However, after successive serial transfers on this medium (after 1 week's growth) and then incubation in the MID medium there was a visible reduction in the coloration of the medium e.g. going from reddish brown in the original culture to having virtually no pigmentation after 2–3 or 4 transfer. Furthermore, taxol production also steadily declined until only ca. 118 ng taxol/l was produced after 5 transfers.

*Wollemia nobilis* (Wollemi pine) is a recently discovered new taxon belonging to the family Araucariaceas. The closest relatives of this tall, monoecius, glabrous tree were through to have become extinct 60–70 million years ago (Royal Botanic Gardens, Sydney, unpublished data). In 1994, David Noble discovered a stand of 20 mature trees and about 20 immature trees growing in a remote part of the Wolemi National Park in the Blue Mountains northwest of Sydney, Australia.

The Wollemi pines are found emergent above a warm temperature rain forest dominated by Coachwood and Sassafras. They occur in a deep sheltered gorge surrounded by sandstone cliffs. The local microclimate is wet with a continuous flowing stream and an understory of ferns. Birds apparently frequent the area, feed on seed produced by these trees. It seems all tree species are host to one or more endophytic fungi. However, commonly, tree species that are growing in damp environments may be host to many endophytic fungal species. This is especially true of the genus Taxus and more recently Taxodium. Some of the most common fungal genera isolated from these trees are species of Pestalotia and Pestalotiopsis. Isolates of this group, regardless of the source from which they are obtained produce the well-known and important anticancer drugtaxol.

If one accepts the hypothesis that endophytic fungi of Taxus may have acquired genes for taxol production from Taxus spp., it is conceivable that such taxol-producing fungi may be found in may plants worldwide given the wide means of dispersal, possessed by fungi. Thus, even though the Wollemi pines are in an area well removed from the natural stands of *Taxus baccata* (Europe—IndoEurope), *Taxus wallachiana* (Nepal, Bhutan India), *T. chinensis* (China), and *T. cuspidata* (Japan), there is likelihood that endophytic fungi from Taxus and other species may have found ingress into this isolated and unique stand of rare and endangered trees. The methods of isolating endophytic fungi from small limb samples of *W. nobilis* are described below. The methods of culturing such fungi, extracting and testing culture extracts for the presence of taxol, and the unequivocal demonstration of the presence of *Pestalotiopsis guepinii* (Desm.) Steyaert in *W. nobilis* and its ability to produce taxol yeis also presented. Furthermore, some scanning electron microscopic observations are reported which show the unique biology of this fungus and we speculate about its dispersal by tropical birds.

Branch samples (1 cm dia×20–30 cm length) of *W. nobilis* were obtained in the summer season from low hanging limbs of mature trees in their native range. The ends of each twig were wrapped in parafilm and the samples shipped by express mail to Montana State University. The samples were stores at 60° C. for 2–3 days prior to processing.

Endophytes of *Wollemia nobilis*

These fungi were isolated from the surface treated (70w ethanol for 10 sec and then placed in a flame to remove excess ethanol) stems and leaves by carefully sampling the phloem/cambium (designated b) and xylem tissues (designated x). Leaves (designated f) were also surface treated with ethanol, as above, and the mesophyll and palisade layers were obtained. Small pieces of plant tissue excised with a sharp blade were placed on water agar in Petri plates. After several days, individual hyphal tips of the fungal colonies were removed and placed on potato dextrose agar (PDA), incubated for 10 days, and periodically checked for culture purity. Eventually, each culture type was again transferred, by the hyphal tip method, to a water agar plate containing small pieces of sterilized carnation leaves. These gamma-irradiated leaves commonly permit the development of fungal fruiting structures which aid in their identification. The fungal isolates were numbered and stored in distilled $H_2O$ at 4° C. as agar plugs or in 15% glycerol at −70° C. as spores and mycelium. Each isolate was placed in the Montana State University Mycological collection as a living culture.

Fungal Identification and other Mycology Studies

Fungal spores and fruiting bodies appearing on the carnation leaf fragments were examined by stereo and light microscopy and comparisons made with standard mycological reference sources. Measurements were taken and identifications were made. Comparisons of culture characteristics were made by standard methods after growing the organisms on PDA at 23° C. Fruiting structures were fixed and processed using the methods of of Upadhyay et al. (*Mycol. Res.* 95: 785–791, 1991), except that they were placed in 2glutaraldehyde in 0. 1M sodium cacodylate buffer (pH 7.2). These samples were critical point dried, gold coated with a sputter coater, observed and photographed with a JEOL 6100 and JEOL 840A scanning electron microscopes (SEM). Laser scanning light micrographs were taken with a Zeiss confocal laser scan microscope (LSM) equipped with an Argon laser with 4 nm and 514 nm wavelengths. Dry wing feathers of a green-checked conure, *Pyrrhura molinae* (Massena and Souance), and a cockatiel, *Nymphicus hollandicus* (Kerr), were passed over the surfaces of acervuli of *P. guepinii*. Attempts were made to dislodge spores from some features with jets of inert dusting gas. Feathers were gold coated and examined in JEOL 840A and JEOL 6100 scanning electron microscopes. Conure features which were exposed to the spores were also soaked in distilled water for 1 h, fixed for 1 h in 2% glutaraldehyde in sodium cacodylate buffer, (pH 7.2–7.4), dehydrated in a graded ethanol series, critical point dried, and gold coated before examining with SEM.

Fungal Culturing and Taxol Isolation

The fungi were grown in two liter Erlenmeyer flasks containing 500 ml of MID medium supplemented with 1 g of isoytone per one liter. After 3 weeks of still culture at 23° C., the culture fluid was passed through four layers of cheesecloth to remove solids and the preparation was treated as previously described. After methylene chloride extraction the extract of each fungal isolate was examined for the presence of taxol by an immunological method. In the case of isolate W-lf-2, at least 10 L of culture fluid were obtained and then taxol was isolated and purified in the fluid by standard methods. This fungus was chosen for study because of its relatively high production of taxol as determined immunologically on culture extracts.

Thin Layer Chromatography (TLC)

All comparative TLC analyses were carried out on Merck 0.25 mm silica gel plates developed in solvents A: chloroform/methanol 7:1 v/v, B : chloroform/acetonitrile 7:3 v/v, C: ethyl acetate/isopropanol 95:5 v/v, D: methylene chloride/tetrahydrofuran 6:2 v/v and E: methylene chloride/methanol/dimethylforamide (90:9:1 by volume). Taxol was detected using a spray reagent consisting of 1% vanillin in sulfuric acid after gentle heating. It appears as a bluish spot fading to dark gray after 24 h.

Spectroscopic Analyses

After isolation from fungal cultures, the putative taxol was dissolved in 100% methanol and the UV spectrum scanned in a Beckman D-50 spectrophotometer. Electrospray mass spectroscopy was done on samples dissolved in methanol, water, acetic acid 50:50:1 (by volume). It was injected with a spray flow of 2 $\mu$L min$^{-1}$ with a spray volume of 2:2 KV via the loop injection method.

Taxol Immunoassays

The extracts (50 mg/mL) were centrifuged in a microfuge (10 min) to remove insoluble material. Taxol assays were carried out by competitive inhibition enzyme immunoassay (CIRIA) using a taxol immunoassay kit (Hawaii Biotechnology Group, Aiea, Hi.) as per the manufacturer's instructions. Detection was by an alkaline phosphatase reaction, with standardization by a curve constructed with taxol standard supplied with the immunoassay kit. The assay sensitivity was given as +/−ng/mL taxol.

Endophytic Fungi

There was recovered at least 11 isolates of endophytic fungi from W. nobilis from the several small twigs that were sampled. There were five isolates of Pestalotiopsis spp. recovered. Several other fungal genera were also isolated including Xylaria and Penicillium as well as several unidentifiable fungi (Table 5). Each fungus was grown in the standard medium, extracted as described, and assayed for taxol. Of the fungi studied, the one of greatest interest was W-lf-2 since it produced the largest amount of taxol (Table 5). W-lf-2 possessed fusiform conidia having four septa with hyaline terminal cells and a brownish coloration in the three median cells which is best seen by laser confocal microscopy. Each spore consistently had one terminal appendage at the proximal end and 2–3 at the apical end. The conidia from this organism averaged 5–6 $\mu$m and 15–18 $\mu$m when obtained from acervuli produced on carnation leaves. This fungus (W-lf-2) was tentatively identified as *Pestalotiopsis guepinii*, and this was confirmed by Dr. G. Kinsey of the International Mycological Institute, Surey, England (IMI 371184). This isolate may be considered a variant of *P. guepinii* because of these subtle spore decoration differences. Furthermore, it is to be noted that there are many species listed for Pestalotiopsis whose descriptions overlap and the whole genus requires revision of *P. guepinii*.

The behavior of *P. guepinii* (W-lf-2) spores under different conditions of development, humidity and processing was also noted. Characteristically, when the conidia of *P. guepinii* are formed they are turgid, but as cultures dried, conidia, both in carnation leaf tissue and on the culture media, shriveled. When placed in distilled water they became turgid in a few seconds. However, in various spore, mounting media, such amann's, it took 1–2 h for spores to become turgid. Spores from dried cultures often burst after 10–15 min in distilled water. In light microscopic sections young developing conidia characteristically appeared turgid and older spores, even on the same leaf tissue were normally shriveled. These same observations were also made with tissues processed for SEM. However, newly developed spores remained turgid although the hyaline apical and proximal cells sometimes shriveled. However, older spores are more characteristically shriveled. Although some studies have been done on the ultrastructural characteristics of Pestalotiopsis, spore shrinkage and swelling were not discussed. However, these observations are comparable to those recently made on *P. microspora* isolated from Bald Cypress and this behavior may be generally common to species of Pestalotia and Pestalotiopsis. The merits of this unique spore behavior to this group of fungi may have relevance to survival during periods of drought since rehydration (shriveled spores) yields viable conidia.

Evidence for Taxol from *P. quepinii*

The endophyte selected for further examination and evidence for taxol production was W-lf-2, *P. guepinii* (Table 5). This isolate produced >480 ng taxol/liter according to the CIEIA taxol monoclonal specific assay, while other isolates of Pestalotiopsis sp. produced 172 and 127 ng/liter, respectively (Table 5). None of the other endophytes examined produced any detectable levels of taxol (Table 5).

There was prepared 10–12 liters of three week old culture fluid and processed by solvent extraction and chromatographic methods. The compound that was isolated, as a few micrograms, possessed the identical chromatographic properties in all TLC systems and yielded an identical color reaction to authentic taxol. It was never detected in the inoculated culture medium and could not have been carried from the original source tree, since taxol is not present in *W. nobilis*. This fact was established by exhaustively extracting 1 g of *W. nobilis* stems with methylene chloride, and then subjecting the residue, after evaporation to the CIEIA monoclonal immunoassay which gave negative results.

The fungal compound produced an identical electrospray mass spectrum as authentic taxol with the major molecular ion being $(M+H)^+=854$ and an $(M+Na)^+$ ion=876. Furthermore, the compound from the fungus yielded a UV absorption spectrum that was identical to authentic taxol About a 0.1 portion of the purified fungal preparation (putative taxol) yielded 379 ng of taxol via the immunoassay procedure which gives a specific reaction to taxol since the antibodies in the assay are prepared by the monoclonal technique. The combined immunochemical, chromatographic and spectroscopic data suggest that the fungal compound is taxol.

*P. guepinii* Dispersal

It is postulated that fungi may have acquired the ability to produce taxol via horizontal gene transfer from Taxus spp. The view is in contrast to an independent coevolution for the genetic/biochemical mechanisms required for taxol production. Pestalotia and Pestalotiopsis are the most commonly found fungal genera making taxol. Taxol producing isolates of it have been found in bald cypress *Taxodium distichum*. Now, however, how can we possibly account for a taxol producing endophyte being present in an extremely isolated part of Australia, and in one of the world's rarest trees? It was observed that the conidia of *P. guepinii* became attached to hydrophobic surfaces (plastic tubes and pipette tips). Such interactions may also occur between the appendages of *P. guepinii* and the hydrophobic surfaces of birds' features. Dried inoculated feathers were gold coated and examined directly with SEM. Jets of inert dusting gas did not dislodge some of the spores. Spores taken directly from the acervuli were characteristically shriveled and readily adhered to the rachis. Spore appendages appeared to attach tenaciously to the feature. Conidia also readily attached to pinnae and barbules and were often lodged between barbules even after feathers were soaked in distilled water, fixed and critical point dried. Appendages of dried spores were difficult to distinguish, but after they were hydrated and critical point dried they were easily observed against the background of barbules.

It is possible to imagine how a bird preening its feathers may eventually dislodge spores only to have them passed to the tree limb during a beak cleaning exercise. Although the conures are not Australian birds, other parrots which are common to Australia include Rosellas, Cockatoos and the Cockatiel. One source of the *P. guepinii conidia* may have been the yew forests of Nepal, India, China or the Philippines. However, another alternative may be the numerous ornamental yews found in the Sydney area and transfer to the Wollemi pines may have occurred by one of the parrots or other bird species from those areas of the world in which the yews are common.

Since taxol is an antifungal compound demonstrating effectiveness against oomycetous fungi, it may be that other endophytic fungi that also produce this compound may be effective competitors against such fungi as Phytophthora and Phythium. Thus, there may not be any unique biological feature of the Wollemi pine, other than its moist environment that allows it to be a host to *P. guepinii*. Many plant species in Australia may support the growth of endophytes producing taxol.

TABLE 5

Taxol production of various endophytic fungi isolated from several small stems of the Wollemi pine in eastern Australia.

| Culture Number | Identification | Dry Weight of extract (mg/L$^{-1}$) | Taxol Total |
|---|---|---|---|
| W-If-1 | *Pestalotiopsis sp.* | 100 | 172 |
| W-If-2 | *Pestalotiopsis guepinii* | 195 | 485 |
| W-If-6 | *Pestalotiopsis sp.* | 64 | 0 |
| W-x-3 | *Pestalotiopsis sp.* | 98 | 127 |
| W-x-1 | *Pestalotiopsis sp.* | 64 | 0 |
| W-b-14 | *Xylaria sp.* | 47 | 0 |
| Wp-2 | *Penicillium sp.* | 133 | 0 |
| Wb-3 | unidentified | 41 | 0 |
| Wb-6 | unidentified | 21 | 0 |
| Wb-7 | unidentified | 10 | 0 |
| W-b-9 | unidentified | 15 | 0 |

An example of a taxol microbial culture medium is set forth below in table 6.

TABLE 6

Taxol Microbial Culture Medium (high sugars)

| | g/liter |
|---|---|
| glucose | 1 |
| fructose | 3 |
| sucrose | 6 |
| Na acetate | 1 |
| casein amino acids | 0.5 |
| KH$_2$PO$_4$   pH 6.8 | 1 ml of 1M |
| | mg/liter |
| vitamins | |
| thiamine | 1 |
| biotin | 1 |
| pyridoxal | 1 |
| calcium pantothenate | 1 |
| sodium benzoate | 10–100 |
| MgSO$_4$ | 3.6 |
| Ca(NO$_3$)$_2$ | 6.5 |
| Ca(NO$_3$)$_2$ | 1 |

TABLE 6-continued

Taxol Microbial Culture Medium (high sugars)

| | |
|---|---|
| ZnSO$_4$ | 2.5 |
| MnCl$_2$ | 5 |
| FeCl$_2$ | 2 |

TABLE 7

Growth and bulbil formation of *Taxomyces andreanae* on various tree species normally growing in the vicinity of *Taxus brevifolia*. All observations were recorded 1 week after inoculation with a 1.0 × 1.0 agar block supporting fungal growth.

| | Av growth from edge of agar block (cm) | | Formation of bulbils* | |
|---|---|---|---|---|
| Plant Species | Twigs/leaves | Bark | Twigs/leaves | Bark |
| *Taxus brevifolia* Nutt. Pacific Yew | 2.0 | 0.25–0.5 | heavy | heavy |
| *Betula nigra* L. River Birch | 1.0 | 0.75 | heavy | mod-erate |
| *Pinus monticola* Dougl. Western white, pine | 0.1 | 0.2 | light | light |
| *Tsuga heterophylia* Rafn Sarg. Western Hemlock | 0.0 | 0.1 | none | none |
| *Pseudotsuga taxifolia* (Poir) Britt. Douglas fir | 0.1 | 0 | none | none |
| *Thula pilcata* Donn Western Red Cedar | 0.5 | 0.5 | light to moderate | heavy |
| *Picea engelmanni* Parry ex Engelm. Engelmann spruce | 0.1 | 0 | moderate | none |
| *Larix occidentalis* Nutt. Western larch | 0 | 0 | none | none |

*Bulbil formation is given in terms of heavy (completely covering the area where mycelium is growing) to moderate, to light (little or sparse bulbil formation).

The fungi according to the present invention, when grown in a defined medium, use sodium benzoate 10–100 mgs/liter to recover the taxol from the medium. The fungi are preferably maintained as an inoculum source in a freshly prepared malt agar (100 mgs of benzoate/liter)

The fungi do not grow well on shake culture. The optimal fungal growth occurs on bactosoytone 5–7 grams/liter (instead of peptone include the essential amino acids and fructose and glucose). With 10 grams sucrose, together with benzoate, vitamins and minerals as per Taxol Microbial culture medium. To further confirm the presence of taxol and baccatin in fungal preparations and extract, a culture of *T. Andreanae* was prepared by CHCl$_3$/MeOH extraction, prepared TLC on CHCl$_3$/acetonitrile 7:3v/v followed by elution of a 1 centimeter wide area at R$_F$0.18–0.25. Then the residue was subjected to a micropore HPLC separation from optimum sensitivity. The study was conducted on LC/MS using a reverse phase column (1 mm)×150 mm×5 µm particles with an Isocratic mobile phase consisting of 65 percent acetonitrile/35 percent 2 mM ammonium acetate at a flow rate of 50 microliters/minute. Subsequent analysis of two microliters of the sample prepared from 100 microliters of the dissolved sample prepared from 100 microliters of the dissolved sample yielded a peak with the retention time identical to taxol (7.85 minutes) and 6.4 minutes consistent with the pseudomolecular ion (M+NH4)+baccatin III.

Figure 3:
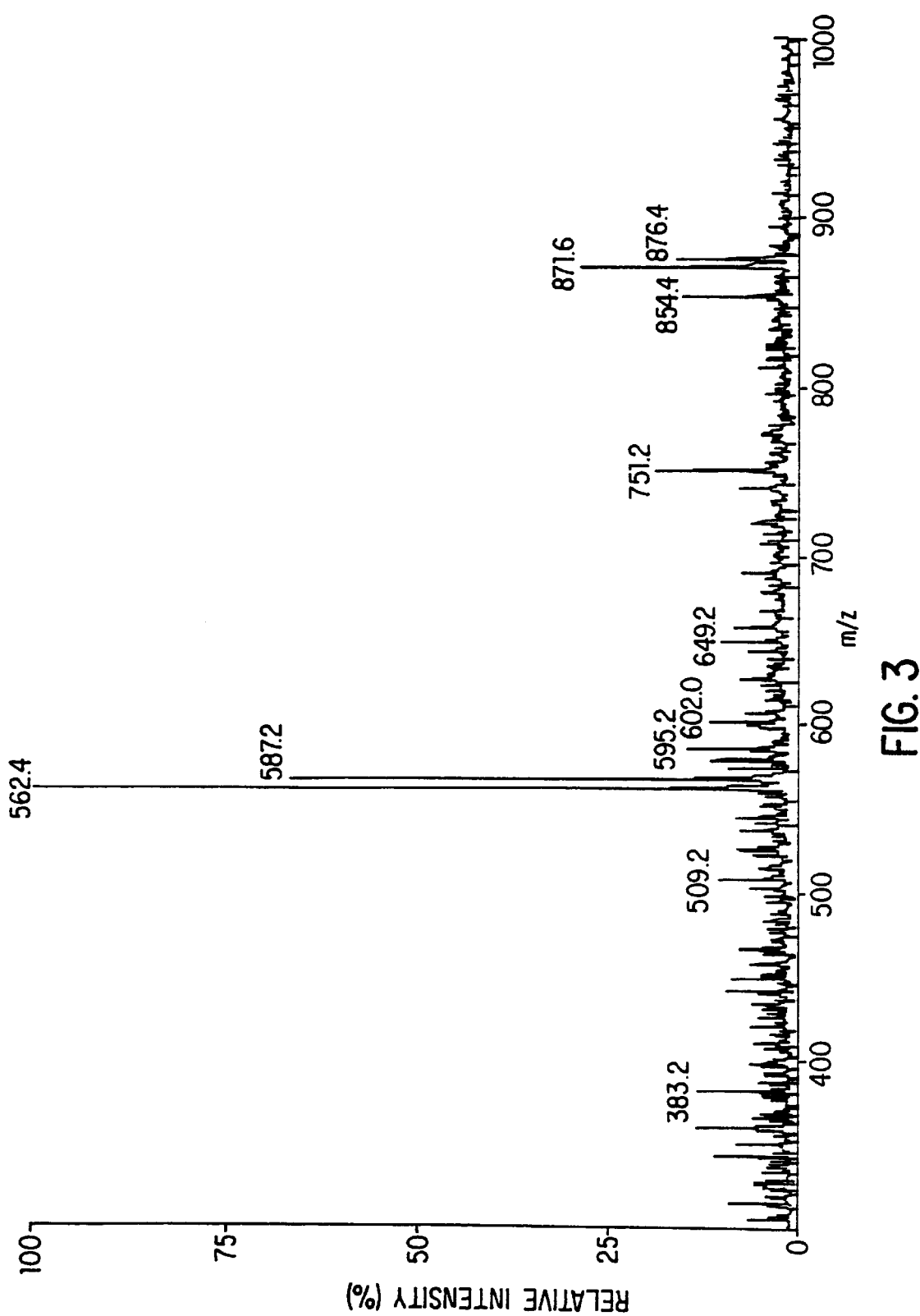
FIG. 3 shows a flow injection ion spray mass spectrum of TLC fraction RF 0.18 of fungus extract after injections of diluent wherein the low intensity ions consistent with taxol are m/z 854 and 871.

FIG. 3 illustrates the mass spectrum of the taxol eluting peak at 854–871 consistent with taxol. The amount of taxol produced in this particular medium is approximately 1 microgram/liter of the medium.

This does not represent endogenous taxol from the yew tree for several reasons. Radiolabeling experiments with phenylalanine, sodium benzoate or acetate $^{14}C$ as precursors yields radiolabelled taxol. Accordingly, the experiments clearly show that the taxol is being synthesized.

To further describe the *Taxomyces andreanae* microbe, the following detailed examples are provided.

EXAMPLE 1

*Taxomyces andreanae* is a novel endophytic fungus associated with the inner bark of *Taxus brevifolia* Nutt. (Pacific Yew). This fungus has small hyphae which average 1.2 µm in diameter. It characteristically forms clumps of loosely constructed cells (bulbil-like). These clumps of various shapes and sizes typically range from about 5×5 to 16×30 µm in diameter and length. The cells in these clumps average about 1.5×2.5 µm and appear to be loosely packed in the bulbi and are incapable of germination. This fungi grows rapidly on many common laboratory media, covering the plates with its mycelium in three or four days. It lacks clamp connections and dolipore septations. Its telemorph is unknown. The Taxomyces andreanae is a endophytic hyphomycete, isolated exclusively from the inner bark on small limbs of a specific yew tree in northern Montana.

The fungus species were isolated from the upper limbs of a shrub-like Pacific yew tree growing as undercover in a mature undisturbed cedar forest in Flathead County, Montana. Small limbs (0.5–1.0 centimeter) were surface treated with 70 percent ethanol. The outer bark was peeled back and pieces of the white inner barks (phloem/cambium) were aseptically removed and placed on $H_2O$ agar. Hyphal tips of fungi growing from the pieces of the plant were placed on mycological agar and fungal growth was enhanced. The growth pattern of the fungus was studied on other plant species. Leaf, stem, and bark samples of various plant species growing near the tree from which this fungus was obtained were collected near the Hungry Horse dam site in the Flathead National Forest. Small pieces (0.5–2 cm) of leaves, stems and barks of these species were placed over four layers of cheesecloth, thoroughly dampened, and autoclaved. Agar blocks (1.0×1.0 cm) supporting fungal growth were then placed on the sterilized plant material and fungal growth was observed and measured after one week. The growth of the fungus was measured daily after placement of 0.5×0.5 cm agar blocks on standard freshly prepared agar media plates (Difco), e.t., potato dextrose broth afar, nutrient agar, oatmeal agar, cornmeal agar, lima bean agar, water agar, and malt agar.

EXAMPLE 2

Agar blocks having mycelia and bulbil-like structures were fixed and dehydrated as for transmission and scanning electron microscopy (SEM) (FIGS. 6, 7, 8, and 9). For SEM, the material was then critical point dried, gold coated and sputter coated, and observed with a JEOL 840A scanning electron microscope. Fungal structures were measured on SEM micrographs after critical point drying of tissues.

This drying procedure caused some shrinkage of biological structures (about 10 percent) which means that they were probably slightly larger, and the clumps of cells more tightly packed than in the living state.

EXAMPLE 3

Taxonomic Treatment and Description *Taxomyces iandrednae* S1; Strobel, Otierle and Hess gen. et ap. nov. (FIGS. 4–9). A pure culture species was obtained of Montana BA which was named *Taxomyces andreanae* S1. This microbe producing taxane was obtained from the above screening. Its structures are described as follows.

Fungus endophyticus e cortice interiora *Taxo brevifolo* Nutt.; hyphae dimporphae—parvae 1.25 µm et magnae ca 3.75 µm latae et longae; bulbilus cellularum ca 1.25×2.5 µm et laxe continguus et apparenter non germinans; mycelium celiter crescens, hyphis fibulis nullis et doliporis septis nullis; telemorphus ignotus.

Mycelium superficial, composed of a network of highly branched, septate, usually hyaline, smooth walled hyphae.

Figure 4:
FIG. 4 shows a scanning electron micrograph of hyphae and fructigenous hyphae of *T. andreanae;* Bar equals 10 μm.
Figure 5:
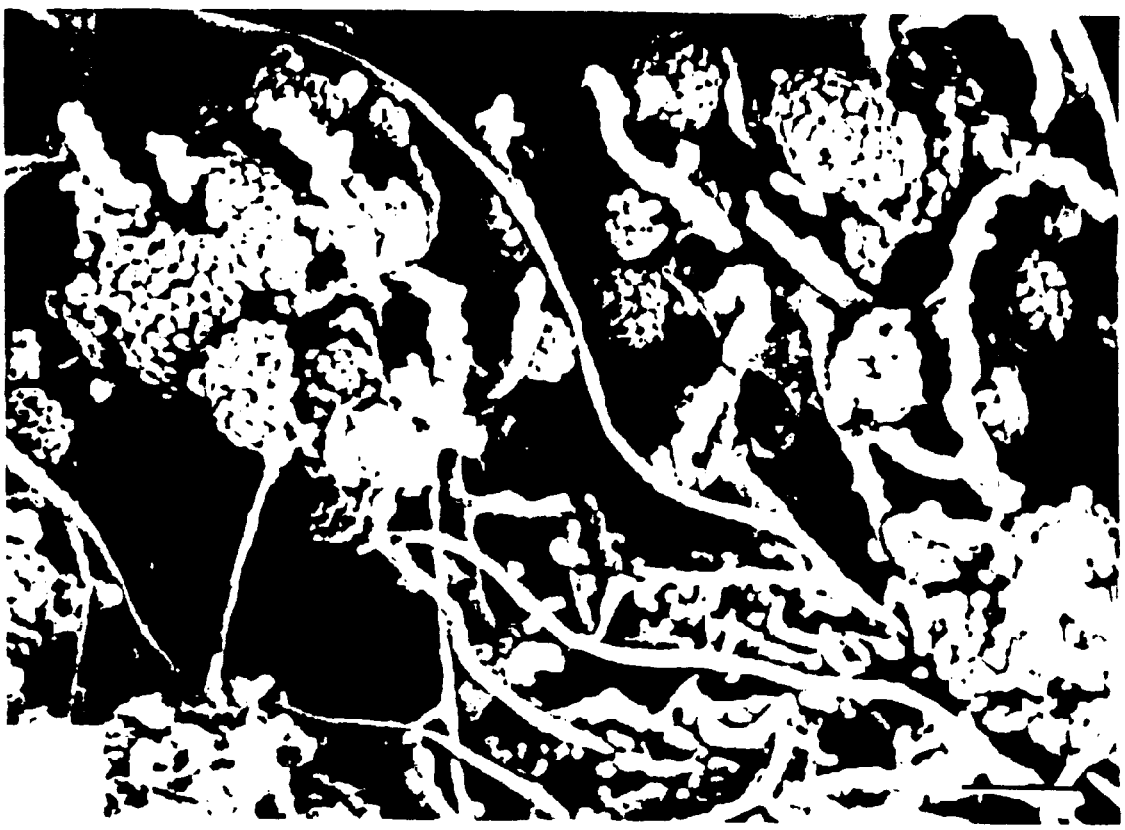
FIG. 5 shows a scanning electron micrograph of a series of various shape bulbils of *T. andreanae;* Bar=10 μm.

Smaller hyphal cells average 1.25 µm in diameter. Larger cells average 3.75 µm in diameter (FIGS. 4–5). Cells are budded from fructigenous hyphae forming clumps which vary enormously in shape from spherical to ovoid to longiform and in size from 5×5 µm in length (for elongate bulbils). Bulbil cells remaining colorless. The cells seem to be loosely packed in the bulbil and are ovoid ca. 1.5×2.5 µm and are never observed to germinate.

Figure 6:
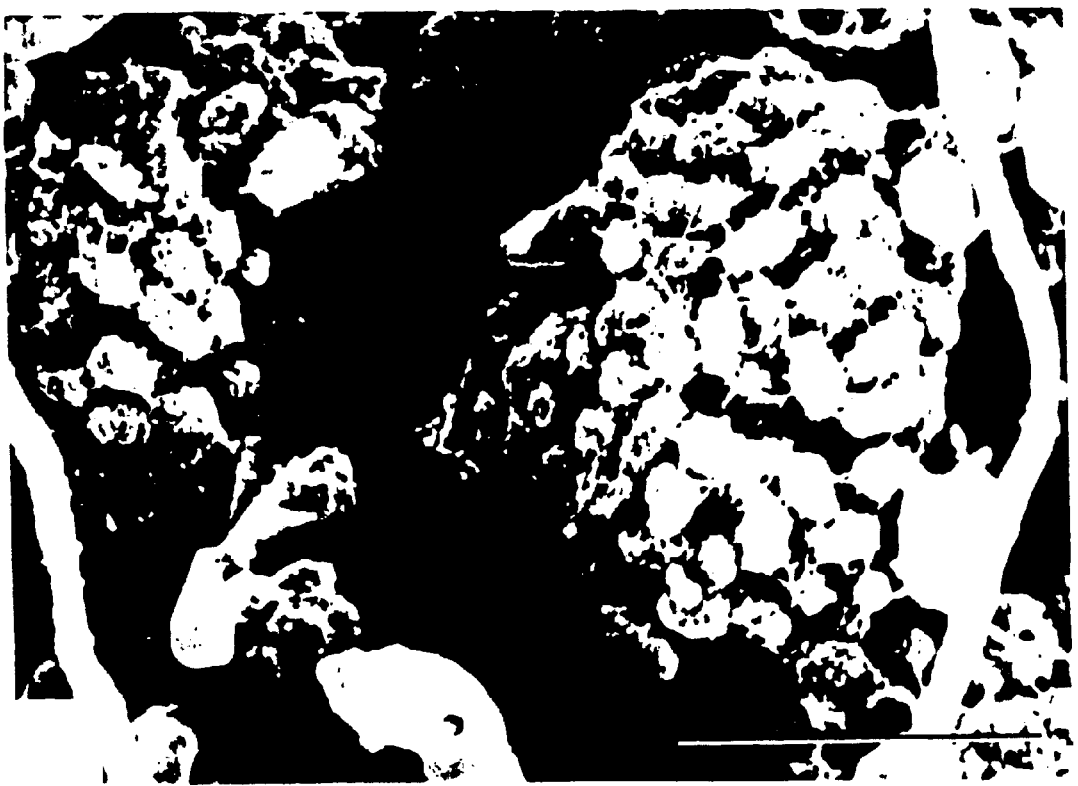
FIG. 6 shows a scanning electron micrograph of single bulbil of *T. andreanae* illustrating the organization of the cells of the bulbil; Bar=10 μm.
Figure 7:
FIG. 7 shows the growth of *T. andreanae* on the inner bark of Pacific yew (left) and growth and bulbil formation on the leaves in small lymph fragments of *T. andreanae* (right).
Figure 9:
FIG. 9 shows the transmission electron micrograph of *T. andreanae* bulbil cells at a higher magnification. Note that the cell wall has two distinct layers, and a fibrous material between the cells; Bar=1 μm.

The "clumps" of cells in FIGS. 5 and 6 are not located on sterismata, but seem to arise by a "budding process" (FIG. 6). Number of cells in each clump varies widely (FIGS. 5 and 6). These "clumps" are referred to as bulbils after the broad definition of deBary (Comparative Morphology and Biology of the Fungi, Mycetozoa and Bacteris, "English Translation, Clarendon Press, Oxford), that is, "small pluricellular bodies incapable of germination" . In *T. andreanae*, the cells of the bulbils, unlike most bulbilliferous fungi, appear to be loosely packed, but nevertheless connected with fibrous material (FIGS. 6, 9). These clumps of cells might also be considered as conidial masses but since germination has never been observed (in sterile $H_2O$ and nutrient broth), the clumps of cells seem to better fit the broad description of a bulbil.

Figure 8:
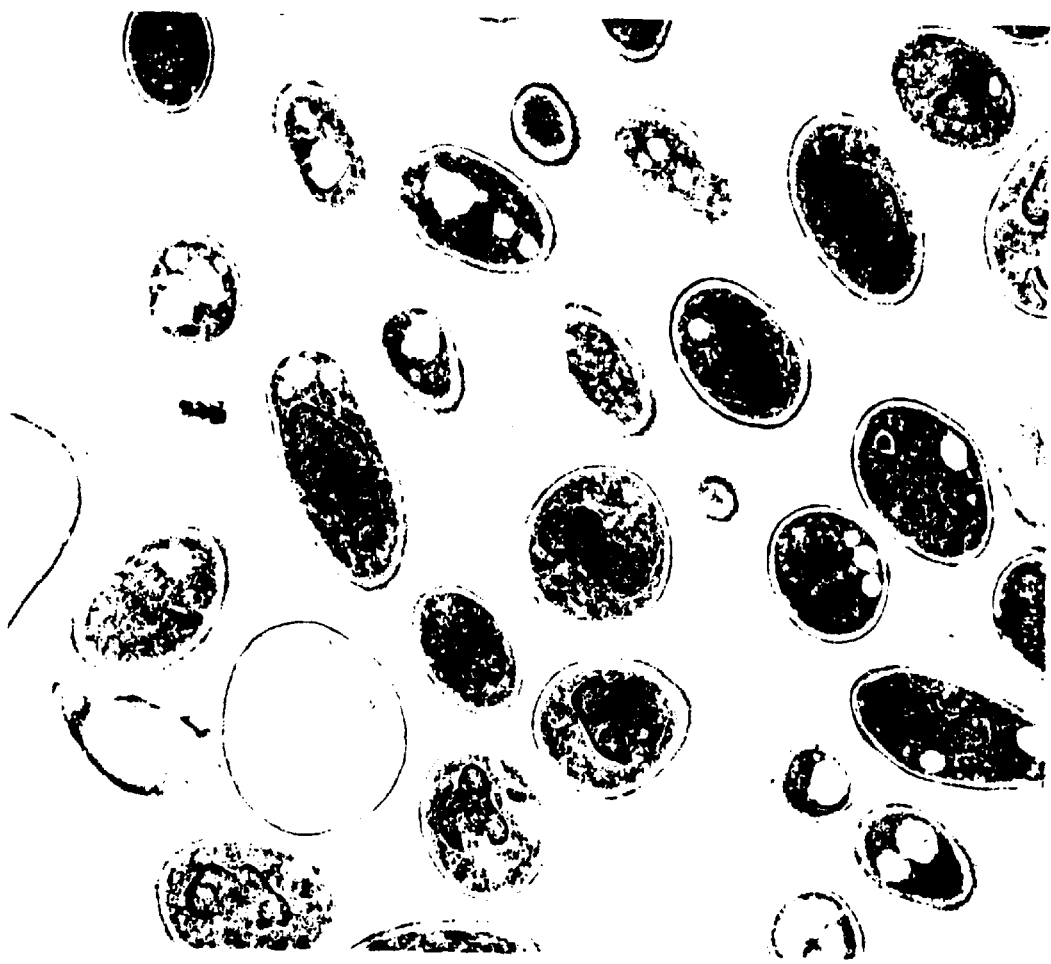
FIG. 8 shows the transmission electron micrograph of bulbil cells of *T. andreanae* illustrating a dense cytoplasm in each cell; Bar=1 μm.

Furthermore, transmission electron microscopic examination of these bulbil cells reveals that they are engorged with cytoplasmic structures including lipid bodies (FIGS. 8, 9). They also possess a bilayered cell wall (FIGS. 8, 9). Nevertheless, these bulbils differ from the bulbils of other standard bulbilliferous fungi by lacking pigmentation, certain sclerotial-like qualities (outer rind-like cells and inner swollen cells) and in the manner of their formation.

EXAMPLE 4

A pure culture species was obtained which was named *Taxomyces andreanae* S2. The fungus species was isolated from the upper limbs of a shrub-like Pacific yew tree growing as undercover in a mature undisturbed cedar forest in Flathead County, Montana as described in Example 1, above. Small limbs (0.5–1.0 centimeter) were surface treated with 70 percent ethanol. The outer bark was peeled back and pieces of the white inner barks (phloem/cambium) were aseptically removed and placed on $H_2O$ agar. Hyphal tips of fungi growing from the pieces of theplant were placed on mycological agar and fungal growth was enhanced.

The growth pattern of the fungus was studied on other additional plant species. Leaf, stem, and bark samples of various plant species growing near the tree from which this fungus was obtained were collected near the Hungry Horse dam site on the Flathead National Forest. Small pieces (0.5–2 cm) of leaves, stems and barks of these species were placed over four layers of cheesecloth, thoroughly dampened, and autoclaved. Agar blocks (1.0×1.0 cm) supporting fungal growth were then placed on the sterilized plant material and fungal growth was observed and measured after one week. The growth of the fungus was measured daily after placement of 0.5×0.5 cm agar blocks on standard freshly prepared agar media plates (Difco, e.g., potato dextrose broth agar, nutrient agar, oatmeal agar, cornmeal agar, lima bean agar, water agar, and malt agar.

The fungal culture of *Taxomyces andreanae* S2, was tested and found to produce taxanes by the procedures described above.

EXAMPLE 5

A pure culture species was obtained which was named *Taxomyces andreanae* S3. The fungus species was isolated from the upper limbs of a shrub-like Pacific yew tree growing as undercover in a mature undisturbed cedar forest in Flathead County, Montana as described in Example 1, above. Small limbs (0.5–1.0 centimeter) were surface treated with 70 percent ethanol. The outer bark was peeled back and pieces of the white inner barks (phloem/cambium) were aseptically removed and placed on $H_2O$ agar. Hyphal tips of fungi growing from the pieces of the plant were placed on mycological agar and fungal growth was enhanced.

The growth pattern of the fungus was studied on other additional plant species. Leaf, stem, and bark samples of various plant species growing near the tree from which this fungus was obtained were collected near the Hungry Horse dam site on the Flathead National Forest. Small pieces (0.5–2 cm) of leaves, stems and barks of these species were placed over four layers of cheesecloth, thoroughly dampened, and autoclaved. Agar blocks (1.0×1.0 cm) supporting fungal growth were then placed on the sterilized plant material and fungal growth was observed and measured after one week. The growth of the fungus was measured daily after placement of 0.5×0.5 cm agar blocks on standard freshly prepared agar media plates (Difco, e.g., potato dextrose broth agar, nutrient agar, oatmeal agar, cornmeal agar, lima bean agar, water agar, and malt agar.

The fungal culture of *Taxomyces andreanae* S3, was tested and found to produce taxanes by the procedures described above.

EXAMPLE 6

Cultural Characterization of *Taxomyces andreanae* S1

When an agar plug of inoculum of *Taxomyces andreanae* S1 was placed in the center of most freshly prepared agar plates enriched with various nutrients it grew so rapidly that it reached the edge of the plate in 3 days (cornmeal agar, lima bean agar, nutrient agar, malt agar, oatmeal agar). Bulbils did not form on any of these media up to 6 days after inoculation. However bulbils were noticed on the inoculum piece on the cornmeal agar after 6 days.

Some bulbils were noticed at the edge of the malt agar plate 7 days after inoculation. Numerous fluffy aerial mycelia were especially observed on malt agar and after 6–7 days the mycelium on the malt agar developed a deep reddish-brown coloration and a thick mycelial mat.

When the *Taxomyces andreanae* S1 fungus was placed on the autoclaved leaves, fragments of small limbs and bark taken from various tree species located in the geographical area of *Taxus brevifolia*, the best mycelial growth and bulbil formation occurred on Pacific yew (Table 1, FIG. 4), followed by River birch (Betula nigra) (Table 1). In contrast, there was no growth on, or bulbil formation on *Larix occidentalis*, or *Tsuga heterophylla*, (Table 1). Other species differentially support weak fungal growth and light bulbil formation, e.g., *Pinus monticola, Picea engelmanni* (Table 1) These observations suggest the likelihood that some host preference of *Taxomyces andreanae* S1 exists in nature and that it would be unlikely to be found in and on many species other than Taxus or Betula.

This organism appears to be a saprophyte or endophyte with the latter preferred since it was found in association with living tissue. There is no evident gross pathology of the host tree. Furthermore, attempts to use agar blocks infested with *T. andreanae* placed under the bark of yew also failed to cause any disease .manifestation.

Also, the thicker hyphae ca. 3.75 $\mu$m in dia, typically extended the mycelial mat from one object (leaf or limb fragment or agar block) to another. These might be considered "exploratory hyphae". Careful study of the cultural, mycelial and bulbil characteristics in comparison to other bulbilliferous fungi nicely demonstrated the uniqueness of *Taxomyces andreanae*.

EXAMPLE 7

A fungal microbe designated as PAC-2PD-1 wag inolated from the inner bark of a yew tree and grown on M-1-D medium for three weeks. Obtained were dense woolly cream colored mycelium with an irregular spreading pattern, there were no obvious fruiting. The fungal biotype was endophytic.

The cultured fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under UV (254 angstroms) and sprayed with 1% vanillin in sulfuric acid. A spot with the same $R_f$ and color reaction (blue fading to brown) identical to taxol appeared.

EXAMPLE 8

A fungi microbe designated as H21 NA was isolated from the needles of a yew tree and grown on M-1-D medium for three weeks. Obtained were fine, translucent, taupe-colored mycelium with an irregular spreading pattern, fruiting structures being present as small brown-rounded bodies. The fungal biotype was parasitic.

The cultured fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under UV (254 angstroms) and sprayed with 1% vanillin in sulfuric acid. A spot with the same $R_f$ and color reaction (blue fading to brown) identical to taxol appeared.

EXAMPLE 9

A fungal microbe designated as H15 NB was isolated from needles of a yew tree showing spots on the needles. This microbe was grown on M-1-D medium for three weeks. Obtained were cream colored fine mycelium, there were no obvious fruiting structures and the culture was felt-like in texture. The fungal biotype was endophytic or parasitic.

The fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v.

The resulting plates were examined under UV (254 angstroms) and sprayed with 1% vanillin in sulfuric acid. A spot with the same $R_f$ and color reaction (blue fading to brown) identical to taxol appeared.

EXAMPLE 10

A fungal microbe designated as 1ND was isolated from the needles of a yew tree, grown on M-1-D medium for three weeks. Obtained were green mycelium spores identical to cladosporium sp. The fungal biotype was endophytic.

The fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v.

The resulting plates were examined under UV (254 angstroms) and sprayed with 1k vanillin in sulfuric acid. A spot with the same $R_f$ and color reaction (blue fading to brown) identical to taxol appeared.

EXAMPLE 11

A fungal microbe designated as BAC-lNA-1 was isolated from the needles of a yew tree showing spots on the needles and grown on M-1-D medium for three weeks. Obtained were velvet-like areas on the older mycelial growth and there was no obvious fruiting. The fungi were ground ana extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under UV (254 angstroms) and sprayed with 1k vanillin in sulfuric acid. A spot with the same $R_f$ and color reaction (blue fading to brown) identical to taxol appeared.

The data set forth in Tables 7–9 indicate additional fungi obtained by the method according to the present invention. The fungi described by these data are capable of producing taxol or related taxanes.

Evidence that the fungi obtained by the method of the present invention produce taxol includes thin layer chromatographic (TLC) comparisons of the organic extracts of these fungi against standard taxol in two solvent systems, as well as specific monoclonal antibody analysis of these extracts.

Of the fungal extracts listed below, extracts 4-73-1, 2, 3, 8, 10, 11, and 12 contained metabolites that behaved in an identical fashion as authentic (yew) taxol when examined by thin layer chromatography (TLC) on silica gel using the following solvent systems: 95-5 ethyl acetate-isopropanol, and 7-3 chloroform-acetonitrile. The organic extracts of 4-73-4, 5, 6, 7, and 9 had compounds that exhibited behavior similar to that of taxol.

The differences in TLC behavior obtained above are also reflected in monoclonal antibody testing which confirm that the fungal strains produce taxol or related taxanes. Hawaii Biotechnology Group, Inc. performed monoclonal antibody testing using Competitive Inhibition Enzyme Immunoassay (CIEIA) with monoclonal antibodies which they developed. The monoclonal antibody used to detect taxol had the designation MAB-36C and the monoclonal antibody used for detection of taxane, in general, had the designation MAB-8A10. Thus, two tests were performed which involved an antibody specific to taxol, and an antibody that reacts with generic taxanes.

The data presented in Tables 7–9 sets forth the actual value of taxol and taxanes detected in a given sample by CIEIA (detected) and the value extrapolated per liter of culture volume. The data listed for the 4–73 series in Table 7 indicates taxol producing fungal strains. The values listed under "TOTAL WT." in Table 8 are the same values listed as "Detected" in Table 7.

Also included are the taxol/taxane titers measured for the organic extract of *Taxomyces andreanae* (TA) (4-58) which was analyzed concurrently. These values are lower than usual, and probably reflect the poor growth of this particular batch of the fungus.

All of the data are from fungi grown in media containing bacto-soytone (10 g/L), glucose (30 g/L), sucrose (20 g/L), sodium benzoate (30 mg/L), and sodium acetate (1 g/L). When these fungi were grown in this same media to which 2% yew needle broth was added, the taxol/taxane titers were significantly higher.

The values in Tables 8–10, however, are from extracts which were not adulterated with yew in any way. The production of taxol/taxanes suggested by these data reflects the independent biosynthetic capabilities of these fungi obtained by the method according to the present invention.

TABLE 8

| | | TAXOL | | TAXANE | |
|---|---|---|---|---|---|
| CODE | FUNGUS | Detected (µg/sample) | Extrapolated (µg/L) | Detected (µg/sample) | Extrapolated (µg/L) |
| 4-73-1 | CC45BD | 0.0031 | 0.0183 | 0.4112 | 2.4306 |
| 4-73-2 | CC50NA1 | 0.0031 | 0.0274 | 0.2099 | 1.8597 |
| 4-73-3 | CC50NA2 | 0.0029 | 0.0246 | 0.0099 | 0.0840 |
| 4-73-4 | CC52NC | ND | ND | 0.0069 | 0.0410 |
| 4-73-5 | CC53NA | ND | ND | 0.0016 | 0.0350 |
| 4-73-6 | CC53NA1 | ND | ND | 0.0038 | 0.0274 |
| 4-73-7 | CC53NA2 | ND | ND | 0.0021 | 0.0144 |
| 4-73-8 | CC53NC | 0.0046 | 0.0254 | 0.0184 | 0.1016 |
| 4-73-9 | CC54BA | ND | ND | 0.0043 | 0.0306 |
| 4-73-10 | CC54BE | 0.0032 | 0.0411 | 0.0074 | 0.0950 |
| 4-73-11 | CC57BC2 | 0.0064 | 0.1862 | 0.0078 | 0.2268 |
| 4-73-12 | CC64BB | 0.0035 | 0.0532 | 0.0087 | 0.1352 |
| 4-58 | TA | 0.0080 | 0.0147 | 0.0593 | 0.1093 |

Key:
ND = not detected
TA = Taxomyces Andreanae

TABLE 9

TAXOL SPECIFIC CIEIA

| SAMPLE | | WT. (mg) | ASSAYED TAXOL (ug/ml) | N | TOTAL WT. (g) | (WT/WT) % |
|---|---|---|---|---|---|---|
| 4-62 | A | 6.8 | not detected | | | |
| | B | 8.0 | 0.0093 | 1 | 0.0019 | 0.00002 |
| | C | 7.9 | 0.0440 | 2 | 0.0088 | 0.00011 |
| | D | 7.8 | 0.0314 | 1 | 0.0063 | 0.00008 |
| | E | 7.0 | 0.360 | 1 | 0.0072 | 0.00010 |
| | F | 1.0 | not detected | | | |
| | G | 0.6 | not detected | | | |
| | H | 0.1 | not detected | | | |
| 4-61 | A | 0.8 | not detected | | | |
| | B | 7.0 | 0.213 | 2 | 0.0043 | 0.00006 |
| | C | 7.1 | not detected | | | |
| | D | 7.6 | not detected | | | |
| | E | 7.7 | not detected | | | |
| | F | 8.8 | not detected | | | |
| | G | 7.7 | not detected | | | |
| | H | 8.6 | not detected | | | |
| 4-58 | A | 21.0 | 0.0400 | 2 | 0.0080 | 0.00004 |
| 4-73 | 1 | 4.5 | 0.0155 | 1 | 0.0031 | 0.00007 |
| | 2 | 5.0 | 0.0155 | 1 | 0.0031 | 0.00006 |

TABLE 9-continued

TAXOL SPECIFIC CIEIA

| SAMPLE | WT. (mg) | ASSAYED TAXOL (ug/ml) | N | TOTAL WT. (g) | (WT/WT) % |
|---|---|---|---|---|---|
| 3 | 4.7 | 0.0147 | 1 | 0.0029 | 0.00006 |
| 4 | 5.1 | not detected | | | |
| 5 | 5.0 | not detected | | | |
| 6 | 5.3 | not detected | | | |
| 7 | 4.8 | not detected | | | |
| 8 | 4.6 | 0.0231 | 1 | 0.0046 | 0.00010 |
| 9 | 4.2 | not detected | | | |
| 10 | 5.1 | 0.0158 | 1 | 0.0032 | 0.00008 |
| 11A | 5.7 | 0.0320 | 1 | 0.0064 | 0.00011 |
| 11B | 4.8 | not detected | | | |
| 12 | 4.5 | 0.0173 | | | |

TABLE 10

TAXANE ("generic") CIEIA

| SAMPLE | | WT. (mg) | ASSAYED TAXANE (ug/ml) | N | TOTAL WT. (ug) | (WT/WT) % |
|---|---|---|---|---|---|---|
| 4-62 | A | 6.8 | not detected | | | |
| | B | 8.0 | 0.0383 | 1 | 0.0077 | 0.00010 |
| | C | 7.9 | 0.3595 | 2 | 0.0719 | 0.00091 |
| | D | 7.8 | 0.2314 | 2 | 0.0463 | 0.00059 |
| | E | 7.0 | 0.0569 | 2 | 0.0114 | 0.00016 |
| | F | 1.0 | not detected | | | |
| | G | 0.6 | not detected | | | |
| | H | 0 1 | not detected | | | |
| 4-61 | A | 0 8 | not detected | | | |
| | B | 7.0 | 0.2618 | 2 | 0.0564 | 0.00081 |
| | C | 7.1 | 0.0140 | 1 | 0.0028 | 0.00004 |
| | D | 7.6 | not detected | | | |
| | E | 7.7 | not detected | | | |
| | F | 8.8 | not detected | | | |
| | G | 7.7 | not detected | | | |
| | H | 8.6 | not detected | | | |
| 4-58 | A | 21.0 | 0.2965 ± 0.075 | 4 | 0.0593 | 0.00028 |
| 4-73 | 1 | 4.5 | 2.0560 ± 0.18 | 3 | 0.4112 | 0.00914 |
| | 2 | 5.0 | 1.0496 | 2 | 0.2099 | 0.00420 |
| | 3 | 4.7 | 0.0497 | 2 | 0.0099 | 0.00021 |
| | 4 | 5.1 | 0.0343 ± 0.006 | 3 | 0.0069 | 0.00013 |
| | 5 | 5.0 | 0.0081 | 1 | 0.0016 | 0.00003 |
| | 6 | 5.3 | 0.0191 | 2 | 0.0038 | 0.00007 |
| | 7 | 4.8 | 0.0105 | 2 | 0.0021 | 0.00004 |
| | 8 | 4.6 | 0.0920 ± 0.016 | 3 | 0.0184 | 0.00040 |
| | 9 | 4.2 | 0.0215 | 1 | 0.0043 | 0.00010 |
| | 10 | 5.1 | 0.0372 | 2 | 0.0074 | 0.00015 |
| | 11A | 5.7 | 0.0392 | 2 | 0.0076 | 0.00014 |
| | 11B | 4.8 | 0.0205 | 1 | 0.0041 | 0.00009 |
| | 12 | 4.6 | 0.0446 | 2 | 0.0089 | 0.00019 |

A selected collection of taxol producing microorganisms tested above and further defined below, including 13 fungi and 1 bacterium were deposited with the Agricultural Research Service Culture Collection (NRRL), 1815 North University Street, Peoria, Ill., 61604, U.S.A. under the terms of the Budapest Treaty.

Many of the microbes described in this application, have been isolated from the bark or needles of the northwest Pacific yew tree, *Taxus brevifolia*. Ten of these microbes have been submitted for deposit at the Northern Regional Research Center (NRRL) in Peoria, Ill. The microbes submitted represented distinct morphotypes, i.e., only one representative of the Genus Pennicillium was submitted for deposit, although others have been detected. These are only examples of microbes which produce taxol, others have been obtained by the same method described herein. The deposited cell lines have also been tested using CIEIA immunoassay.

All of these microbes have consistently shown evidence of taxol and/or taxane production based on thin layer chromatograhy data and repeated immunoassay data obtained at both Hawaii Biotechnology Group, Inc. in Aieia, Hi., and in an in-house assay at Montana State University.

All of the data accrued has been obtained either from microorganisms grown in defined synthetic media, containing no yew broth, or in media to which yew broth has been added. In each data. set reported below, media is clearly indicated.

De novo biosynthesis of taxane or taxol by microorganisms 1–14 is shown below. The following descriptions include gross morphology, tissue type, biological activity of organic extract of: liquid culture of a particular microbe grown in mycological broth, and compounds which we have isolated and identified from these extracts.

Biological activity is determined by the concentration disk method: each microbe is tested against 2 gram(+) and 3 gram(−) bacteria, and 2 fungi. Zones of inhibition listed are indications of activity. Brine shrimp cytotoxicity is ascertained by $LD_{.50}$ of extract towards brine shrimp. "No activity" simply indicates that no activity was observed in these tests in the laboratory, not the absolute absence of biological activity.

Fungi: Mold Type

Figure 10:
FIG. 10 shows strain 1ND 1000×magnified by electron microscope.

1. IND—On MID (see Table 1) agar: Very fine, highly branched mycelia with tendency to grow into media. Deep bottle-green, velvety appearance to both conidia and conidiophore. Conidia are ellipsoid, two-celled and catenulate, and form in unbranched chains, length ≈11 m, with 6μm. Does not germinate at 37° C. "Illustrated Genera of Imperfect Fungi" Eds. H. L. Barnett and Barry B. Hunter used to key fungus to Order Moniliales, Genus Bispora. isolated from the needles of a shrubby yew tree on Sep. 7, 1991. Deposited NRRL Mar. 3, 1994, Accession No. NRRL 21210. Bioactivity: brine shrimp cytotoxic. See FIG. 10.

2. H1RE - On M1D agar: Very fine, highly divided, off-white mycelia growing into the medium. Dense, thick pale grey conidiophores cover plate within 7 days. Tentatively identified as Genus Penicillium. Isolated from the roots of a healthy shrubby yew tree. Bioactivity: antibacterial, antifungal, brine shrimp cytotoxic. Compounds isolated to date: phomopsolides. Deposited NRRL Mar. 3, 1994, Accession No. NRRL 21208.

Figure 11:
FIG. 11 shows strain H10BA2 1000×magnified by electron microscope.
Figure 12:
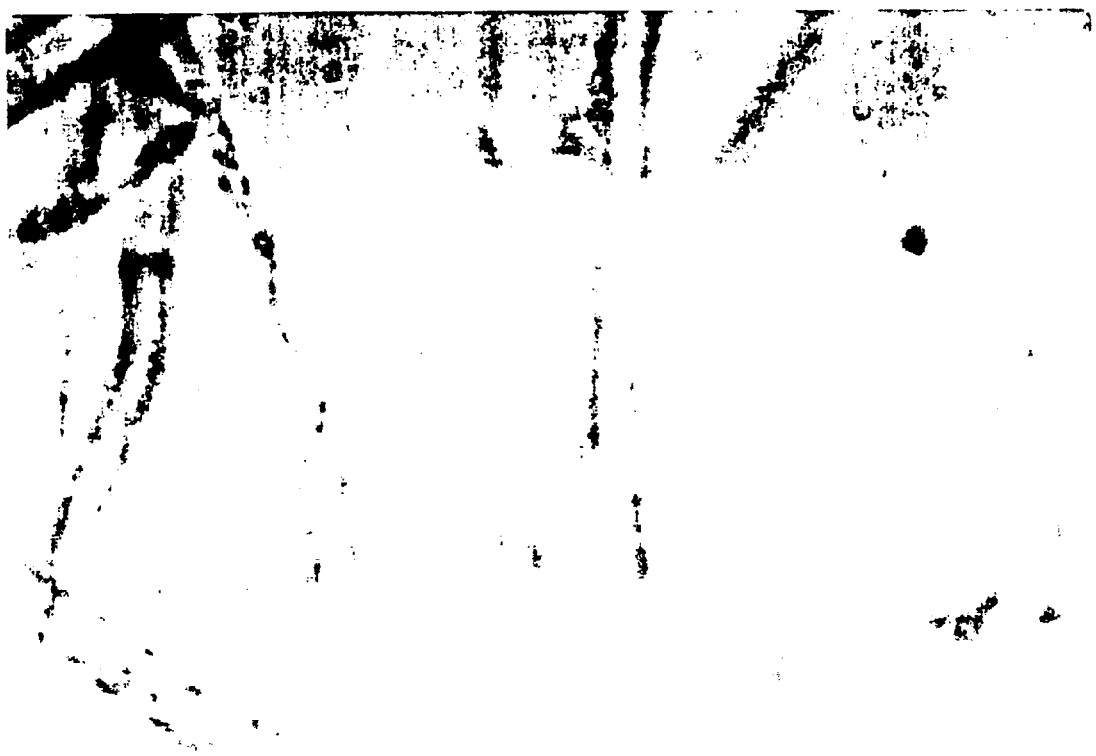
FIG. 12 shows strain WIC65NC 1000×magnified by electron microscope.

3. H10BA2—On M1D agar: Very fine, highly branched off-white mycelia growing down into the medium. Velvety pale green conidiophore with smooth conidia, 2.4×2.4μm. Fungus keyed to enus Penicillium by Dr. Rajinder Siddhu. Isolated from bark of shrubby yew tree. Deposited NRRL Mar. 3, 1994, Accession No. NRRL 21209. Bioactivity: antibacterial, antifungal, brine shrimp cytotoxicity. Compounds isolated to date: penitrem A & B. See FIG. 11.

Figure 13:
FIG. 13 shows strain CC45BD 1000×magnified by electron microscope.

4. CC45BD—On M1D agar: fine, white, branched, septate mycelia, with dark green spores forming after 96 hours. Little or no aerial growth. On mycological agar: mycelia is denser and tends to aerial growth; green spores not formed. Isolated from the inner bark of a 26"yew tree. Deposited NRRL Mar. 3, 1994, Accession No. NRRL 21207. Biological activity: antibacterial. See FIG. 13.

Figure 14:
FIG. 14 shows strain CC50NA1 1000×magnified by electron microscope.

5. CC50NA1—On M1D agar: Off-white mycelia with long, intertwining, branched, septate, filamentous hyphae, and irregular edge. Like *Taxomyces andreanae*, hyphae appear to be of two different sizes. Consistent aerial growth throughout plate gives a "fuzzy" appearance. White bulbils are formed along the length of the hyphae. Isolated from healthy needles of a yew tree. Deposited NRRL Mar. 3, 1994, Accession No. NRRL 21204. Biological activity: antibacterial. See FIG. 14.

6. CC50NA2—similar to CC50NA1, but thicker, fuzzier mycelia.

7. CC50 NB—On M1D agar: Fine, off-white, highly divided mycelia growing into the medium. Deep green velvety conidiophore form after 2 days. Smooth conidia: 4.8×4.8 μm; smooth stipe: 24×4.8 μm, with enlarged apice; metula: 9.6–12.0 μm; phialide: 7.2μm. Keyed to Genus Penicillium. Isolated from healthy needles of a 24" yew tree. Bioactivity: antibacterial, antifungal, brine shrimp cytotoxic. Compounds isolated to date: gliovictin, compactin, griseofulvin, dechlorogriseofulvin, kojic acid.

Figure 19:
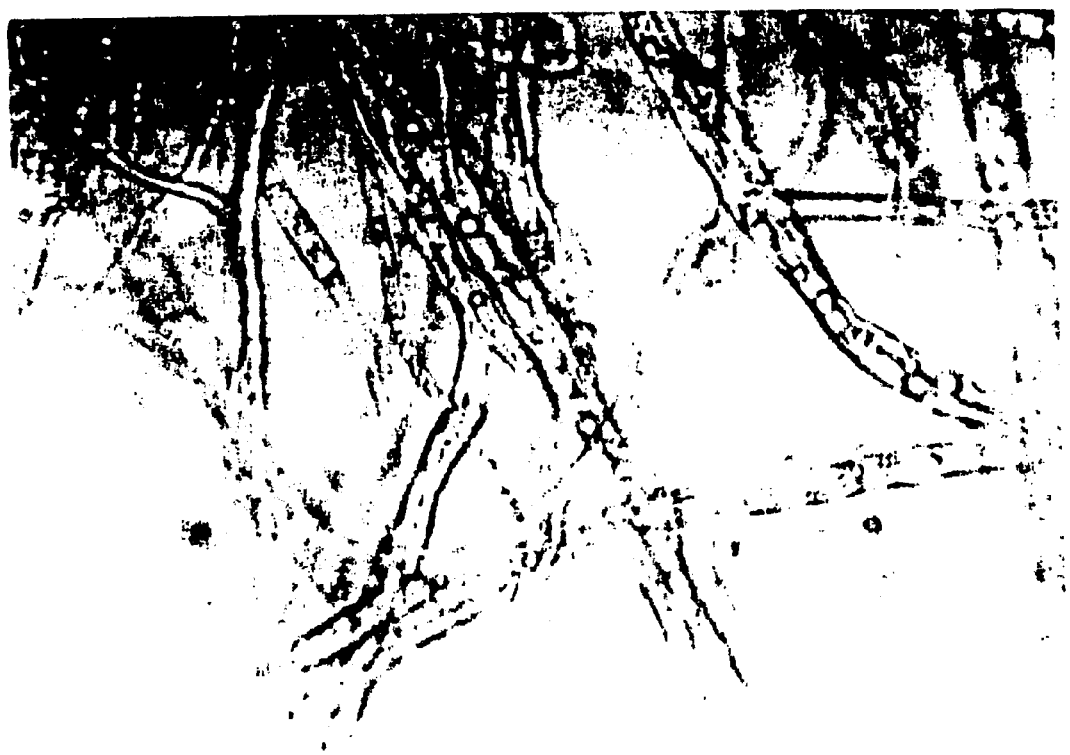
FIG. 19 shows strain CC52NC 1000×magnified by electron microscope.

8. CC52NC—On M1D agar: White, finely divided, highly branched, irregularly edged mycelia with intermittent aerial habit. Aerial hyphae have short "clusters" at regular intervals. Isolated from the healthy needles of a 26" yew tree, Deposited NRRL Mar 3, 1994, Accession No. NRRL 21212. Biological activity: no activity. See FIG. 19.

Figure 18:
FIG. 18 shows strain CC53NA-2 1000×magnified by electron microscope.

9. CC53NA2-1—On M1D agar: Cream colored mycelia with dense, velvety patches of cream to tan, surrounded by deep green, with dark green spores. Thick aerial pycnidia form in cultures after 2 weeks. These are white with a brown core. Tentatively identified as a Xylaria sp. Liquid cultures grown in M1D broth grow quickly and form a thick, syrupy, pink exudate. Isolated from the needles of a 26"yew tree. Biological activity: no activity.
See FIG. 18.

Figure 17:
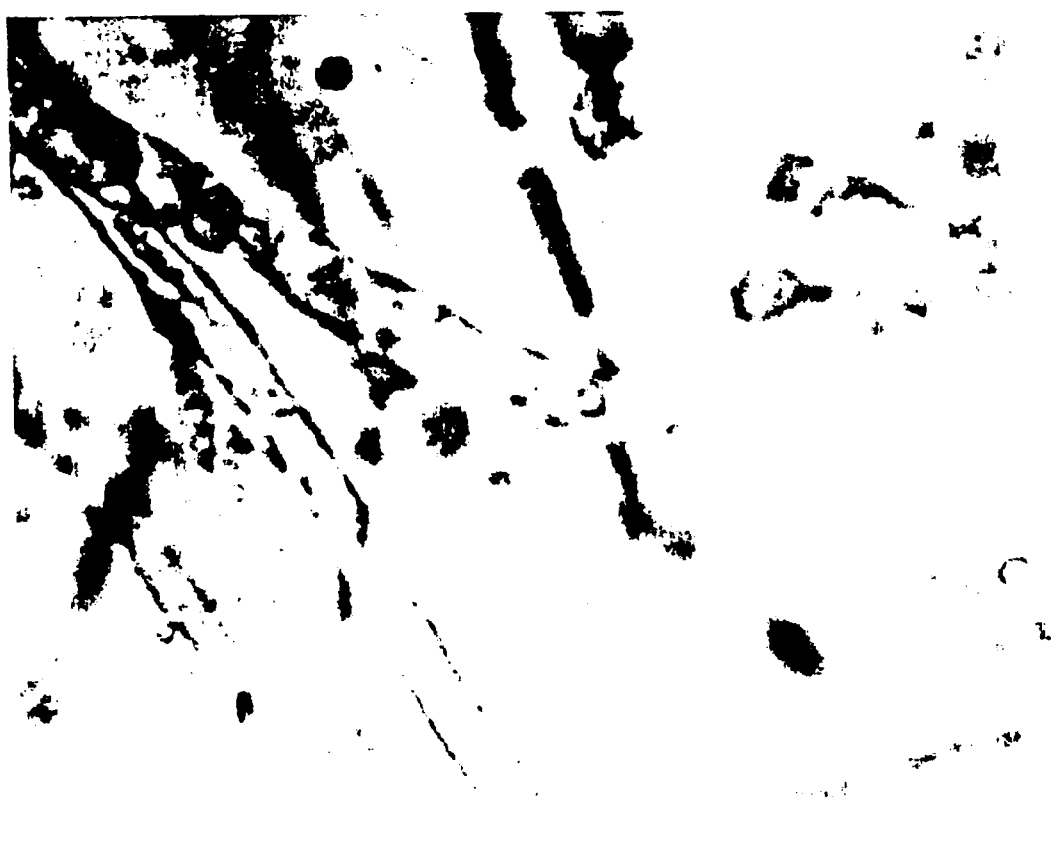
FIG. 17 shows strain CC54BA 1000×magnified by electron microscope.

10. CC54BA—On M1D agar: Dense, fuzzy mycelial mat. consisting of fine, long, thin, branched septate hyphae with terminal and mid-strand budding. Turns rich salmon pink after 5 days. Isolated from the inner bark of an 18 inch yew tree. Deposited NRRL Mar. 3, 1994, Accession No. NRRL 21205. Biological activity: slightly antibacterial, brine shrimp cytotoxic. See FIG. 17.

Figure 15:
FIG. 15 shows strain CC54BE 1000×magnified by electron microscope.

11. CC54BE—On M1D agar: Dense, fuzzy white mycelial mal: with long, thin, sepatate, filamentous hyphae with littler branching. Isolated from the bark of an 18" yew tree. Deposited NRRL Mar. 3, 1994, Accession No. NRRL 21211. Biological activity: slightly antibacterial, brine shrimp cytotoxic. See FIG. 15.

12. CC57Bc-1—on M1D agar: Velvety green appearance, typical of Penicillium sp. The microorganism was isolated from 28" yew tree bark. Bioactivity: antibacterial, antifungal, brine shrimp cytotoxic. Compounds isolated to date: mycophenolic acid.

Figure 16:
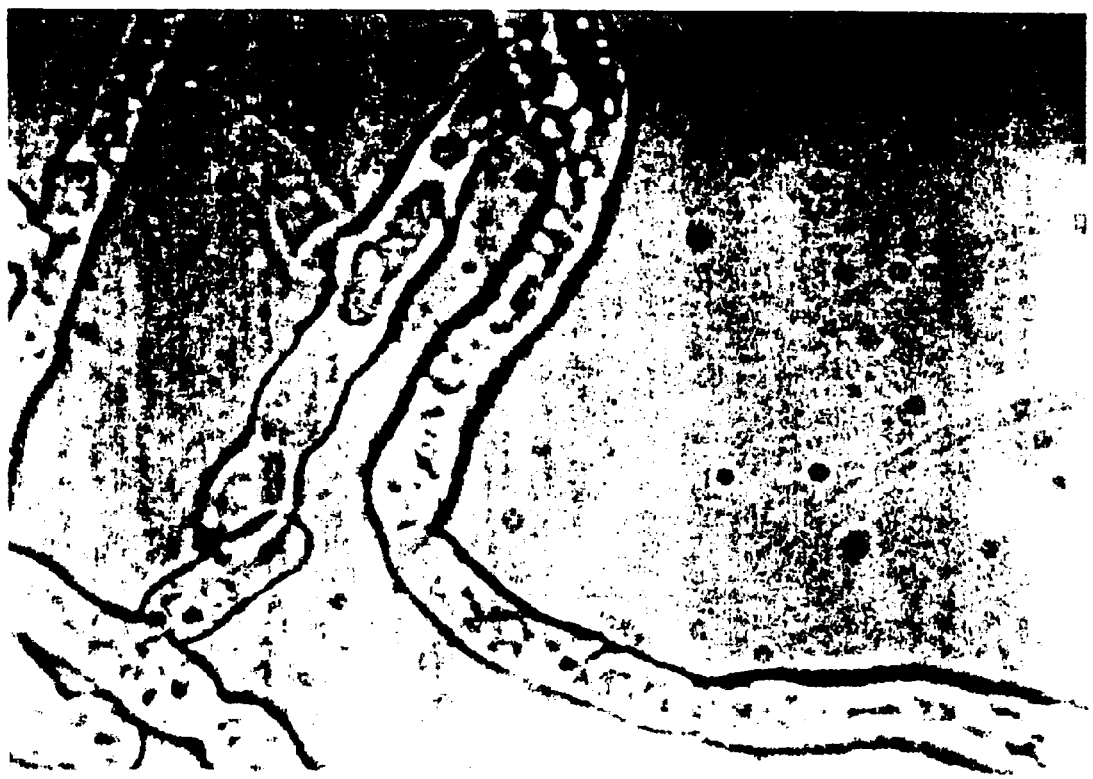
FIG. 16 shows strain CC64BB 1000×magnified by electron microscope.

13. CC64BB—On M1D agar: Fine white mycelial mat consisting of long, thin, branched, septate mycelia. Mycelia develops aerial habit towards edge of late, forming fluffy white Mycelial "clusters" after 5 days of growth. Isolated from 28" yew tree bark. Deposited NRRL Mar. 3, 1994, Accession No. NRRL 21206. Biological activity: antibacterial, brine shrimp cytotoxic. See FIG. 16.

Bacteria

14. CC48BB—On Tryptic soy agar or penassay antibiotic agar: Creamy, regular colonies, gram (+) cocci. Isolated from 18" yew tree bark. Identified by Dr. Eid Megeed as a Micrococcus sp. Biological activity: antibacterial, brine shrimp cytotoxic.

A. Additional CIEIA testing was performed to conform the production of taxol or taxane by the microorganisms. Microbes were grown in mycological broth +2% yew broth, 100 mL each. Taxol and Taxane/L values are extrapolated by multiplying/fraction values by 10 if the entire extract was tested. If only ½ of the extract was tested, then /fraction titer was multiplied by 20 to obtain /L value. The blank medium, which consisted of 1L of uninoculated mycological broth +2% yew broth, obviously did not need extrapolation for the /Liter titer. See Table 10 below.

For all of the fungi we determined taxol and taxane titers in term of ug/l, and ug/g dry mycelia weight. We only determined titers in ug/l for the single bacterium CC48BB.

TABLE 11

| | $CH_2Cl_2$ ext. | taxol/fraction | taxol/liter | taxane/fraction | taxane/liter | Specific activity taxane/dry wt. mycelia (ug/g |
|---|---|---|---|---|---|---|
| CC45BD | 0.0027 | 0.408 ug | 4.08 ug | 1.67 ug | 10.67 ug | 53.35 |
| CC48BB | 0.0045 g | 0.518 | 5.18 | 5.63 | 56.3 | |
| CC50NA1 | 0.0045 | 0.462 | 4.62 | 5.22 | 52.2 | 6.29 |
| CC50NA2 | 0.0022 | 0.880 | 8.80 | 8.96 | 89.6 | 28.90 |
| CC52NC | 0.0024 | 0.758 | 7.58 | 7.96 | 79.6 | 265.33 |
| CC53NA | 0.0012 | 0.622 | 6.22 | 7.27 | 72.7 | 16.16 |
| CC53NC | 0.0020 | 0.614 | 6.14 | 5.65 | 56.5 | 9.74 |
| CC54BA | 0.0074 (½) | 0.304 | 6.08 | 4.20 | 84.0 | 19.53 |
| CC54BE | 0.0056 (½) | 0.174 | 3.48 | 1.82 | 36.4 | 8.88 |
| CC57BC2 | 0.0065 (½) | 0.192 | 3.84 | 3.59 | 71.8 | 21.75 |
| CC64BB | 0.0060 | 0.264 | 2.64 | 1.87 | 37.4 | 19.68 |
| blank (1L) | 0.0057 | 0.95 | 0.95 | 6.61 | 6.6 | |

A. HAWAII BIOTECHNOLOGY GROUP, INC.

Tested microbes grown in mycological broth 2% yew broth, 100 ml each. Taxol and Taxane/l are extraplorated by multiplying fraction values by 10 if entire extract was tested. If only ½ of the extract was tested, then fraction titer was multiplied by 20 to obtain 1 value. The blank mediu, which consisted of 1l of uninoculated mycological broth 2% yew broth, obviously did not extrapolation.

B. The microbes were grown in yew free media to examine the "uninduced" potential of microbes to make taxol/taxanes. Organisms were grown in mycological broth (soytone and

TABLE 12

| | CH$_2$Cl$_2$ sample (g) | total wt. (g) | taxol/sample (ug) | taxol/Liter (ug) | taxane/sample (ug) | taxane/liter (ug) | Specific activity taxane/dry wt. mycelia (ug/g) |
|---|---|---|---|---|---|---|---|
| CC45BD | 0.045 | 0.0266 | 0.0031 | 0.018 | 0.4112 | 2.43 | 2.80 |
| CC50NA1 | 0.0050 | 0.0443 | 0.0031 | 0.027 | 0.2099 | 1.86 | 1.30 |
| CC50NA22 | 0.0047 | 0.0399 | 0.0029 | 0.025 | 0.0099 | 0.840 | 8.96 |
| CC52NC | 0.0050 | 0.0303 | nd | | 0.0069 | 0.042 | 8.571 |
| CC53NA | 0.0050 | 0.1092 | nd | | 0.0016 | 0.035 | 0.016 |
| CC53NC | 0.0046 | 0.0254 | 0.0046 | 0.025 | 0.0184 | 0.102 | 0.120 |
| CC54BA | 0.0042 | 0.0299 | nd | | 0.0043 | 0.031 | 0.023 |
| CC54BE | 0.0051 | 0.0655 | 0.0032 | 0.041 | 0.0074 | 0.095 | 0.081 |
| CC57BC2 | 0.0057 | 0.1658 | 0.0064 | 0.186 | 0.0078 | 0.227 | 0.105 |
| CC64BB | 0.0046 | 0.0699 | 0.0035 | 0.ob3 | 0.0089 | 0.135 | 0.135 | glucose only). The culture volume was 1 Liter, so volume factor was not necessary for estimation of/Liter titers. However, only a portion of extract was used, and this factor was included in the extrapolation to/Liter titers. See Table 12.

C. Fungi were grown in mycological broth without any yew added. 1ND 2L, H10 BA2 was 10 L, CC50 NA1 and CC50NA22 were 1L. Appropriate factors are used to extrapolate to/Liter titers. See Table 13.

TABLE 13

| | CH$_2$Cl$_2$ sample (g) | total wt. (g) | taxol/sample (ug) | taxol/Liter (ug) | taxane/sample (ug) | taxane/Liter (ug) | Specific activity taxanes/dry wt. mycelia (ug/g |
|---|---|---|---|---|---|---|---|
| 1ND | 0.016 | 0.0463 | 0.0029 | 0.0042 | 0.0058 | 0.0083 | 0.002 |
| H10BA2 | 0.0085 | 0.9249 | 0.0015 | 0.0163 | 0.0879 | 0.9565 | 0.143 |
| CC50NA1 | 0.0142 | 0.0499 | 0.0025 | 0.0088 | 0.0067 | 0.0234 | 0.036 |
| CC50NA22 | 0.0135 | 0.0463 | 0.00298 | 0.0102 | 0.0074 | 0.0254 | 0.102 |

D. Fungi were grown in media 1 (soytone, yeast, vitamins) and 2% yew broth in 500 mL cultures. See Table 14.

TABLE 14

| | CH$_2$Cl$_2$ sample (g) | total wt. (g) | taxol/sample (ug) | taxol/Liter (ug) | taxane/sample (ug) | taxane/Liter (ug) | Specific activity taxanes/dry wt. mycelia (ug/g) |
|---|---|---|---|---|---|---|---|
| CC50NA22 | 0.0046 | 0.0146 | 0.0592 | 0.376 | 0.282 | 1.790 | 1.49 |
| CC53NA1 | 0.0093 | 0.0193 | 0.0327 | 0.135 | 0.241 | 1.003 | 1.93 |
| 4BA | 0.0083 | 0.0198 | 0.0576 | 0.274 | 0.377 | 1.798 | 11.99 |
| H10BA2 | 0.0171 | 0.0366 | 0.0135 | 0.058 | 0.276 | 1.189 | 0.175 |
| CC50NA1 | 0.0071 | 0.0137 | 0.173 | 0.669 | 0.279 | 1.077 | 0.598 |
| Blank | 0.0045 | 0.0045 | 0.149 | 0.149 | 0.307 | 0.307 | |

E. H10 BA2 grown in 26 L Mycological broth without added yew broth. Estimate of 1 L titer includes volume factor. See Table 15.

TABLE 15

| | CH$_2$Cl$_2$ sample (g) | total wt. (g) | taxol/ sample (ug) | taxol/ liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---|---|---|---|---|---|---|---|---|
| H10BA2 | 0.0114 | 1.3142 | 0.1389 | 0.600 | 0.16 | 0.107 | 0.316 | 1.4010.244 |
| H | 0.0103 | 0.0442 | 0.1284 | 0.549 | 0.190 | | | |

F. Fungi were grown in 4×100 mL media 1 and 1% yew broth. See Table 14.

Wiernik et al., "Phase I clinical and pharmacokinetic study of taxol", Cancer Res., Vol. 47, No. 9, (May 1, 1987) p. 2486–93. All publications cited herein are incorporated by reference herein in their entireties.

TABLE 16

| | $CH_2Cl_2$ sample (g) | total wt. (g) | taxol/ sample (ug) | taxol/ liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---|---|---|---|---|---|---|---|---|
| CC52NC | 0.0064 | 0.0530 | 0.0923 | 1.910 ug | 2.94 | 0.264 ug | 5.48 ug | 8.431 |
| CC45BD | 0.0040 | 0.0484 | 0.0236 | 0.714 | 0.193 | 0.1655 | 5.006 | 1.353 |
| Blank | 0.0085 | 0.0090 | 0.243 | 0.257 | | | | |

TABLE 17

These samples were 500 ml, media 1 and 1% yew broth.

| | $CH_2Cl_2$ sample (g) | total wt. (g) | taxol/ sample (ug) | taxol/ liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---|---|---|---|---|---|---|---|---|
| CC50NB | 0.0060 | 0.0977 | 0.0063 | 0.206 | 0.089 | 0.0398 | 1.30 | 0.568 |
| CC64BB | 0.0053 | 0.0252 | 0.0243 | 0.231 | 0.481 | 0.0744 | 0.707 | 1.473 |
| 1ND | 0.0102 | 0.0301 | 0.0175 | 0.103 | 0.057 | 0.0728 | 0.425 | 0.233 |
| 4BA | 0.0125 | 0.0194 | 0.3396 | 1.054 | 7.027 | 1.1420 | 3.544 | 23.63 |

TABLE 18

Cultures were grown in 250 mL tryptic soy broth with 1% yew needle broth added.

| | $CH_2Cl_2$ sample (g) | total wt. (g) | taxol/ sample (ug) | taxol/ liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---|---|---|---|---|---|---|---|---|
| CC48BB | 0.0112 | 0.0225 | 0.0143 | 0.115 | | 0.266 | 2.138 | |
| | 0.0106 | 0.0220 | 0.0109 | 0.091 | | 0.245 | 2.054 | |
| Blank | 0.0055 | 0.0055 | 0.0139 | 0.074 | | | | |
| | 0.0066 | 0.0454 | 0.0064 | 0.177 | | 0.007 | 0.193 | |
| | 0.0073 | 0.0465 | 0.0038 | 0.098 | | 0.0051 | 0.130 | |
| Blank | 0.0040 | 0.0331 | 0.0025 | 0.024 | | 0.007 | 0.069 | |

Thus all of the exemplary taxol or taxane producing microorganisms set forth herein were obtained by the general method of the invention and found to produce taxane or taxol.

Taxol produced by any of the above microorganisms can be used in the treatment of cancers, including, but not limited to lung cancer, ovarian cancer, breast cancer, prostate cancer and melanoma, as well as others. See for example, Holmes et al., "Phase II trial of taxol, an active drug in the treatment of metastatic breast cancer", J. Natl. Cancer Inst., Vol. No. 83, No. 24., December 1991, p. 1797–1805; Rowinsky et al., "Cardiac: disturbances during the administration of taxol", J. Clinical.

Oncol., vol 9, No. 9, September 1991, pp. 1704–1712; Brown et al., "Phase I trial of taxol given by a 6 hour intravenous infusion" , J.

Clinical. Oncol., Vol 9, No. 7, p. 1261–67; "Ovarian Cancer" , Semin. Surg. Oncol, Vol. 6, No. 6, p. 328–38; Thigpen et al., "Chemotherapy in ovarian carcinoma: present role and future prospects, Semin. Oncol., vol 16, (4 Suppl. 6), August 1989, p. 58–65; Roytta et al. "Morphological studies on the effect of taxol on cultured human prostatic cancer cells, Prostate 1987, Vol 11 (1), p. 95–106; McGuire et al., "Taxol: a unique antineoplastic agent with significant activity in advanced ovarian epitelial neoplasms" Ann Inter. Med. vol 111 (4), August 1989, p. 273–279. and Taxol is administered in acceptable formulations as Set forth in Remingtons Pharmaceutical Sciences, 18th Ed., incorporated herein by reference. Taxol formula-tions may comprises from about 0.01 to 99% taxol, and may preferably be in dosages of about 50 mg/m2 to about 300 mg/m2, which is the maximum dose-limiting toxicity for peripheral neuropathy. Dosage times known to those of skill in the art may be used. A 6-hour IV infusion every 21 days is preferred.

All publications cited herein are incorporated .by reference herin in their entireties.

Taxol is administered in acceptable formulations as set forth in *Remingtons Pharmaceutical Sciences,* 18th Ed., incorporated herein by reference. Taxol formulations may comprise from about 0.01 to 99% taxol, and may preferably be in dosages of about 50 mg/m2 to about 300 mg/m2, which is the maximum dose-limiting toxicity for peripheral neuropathy. Dosage times known to those of skill in the art may be used. A 6-hour IV infusion every 21 days is preferred.

Due to the pioneering nature of the present invention, one of skill in the art readily recognizes that the present invention also encompasses a process for isolating a fungus which produces e, pharmaceutical product derived from plant material which comprises the steps of:

(a) obtaining tissue fragments from plant material which is the origin of said pharmaceutical product;

(b) placing said tissue fragments on agar medium until fungal growth occurs;

(c) placing fungal hyphae from said fungal growth on mycological agar until a culture in pure form is obtained;

(d) transferring said fungal hyphae to a fungal lab growth medium, and growing a fungal culture;

(e) removing at least a portion of the culture media containing the fungal culture, thoroughly grinding the mycelium, and adding a chromatographic solvent to the mixture;

(f) obtaining a chromatograph of said fungal culture in said chromatographic solvent to form a solution;

(g) checking the solution for presence of the pharmaceutical of interest, and (h) isolating the fungal cultures which produce the pharmaceutical product.

In addition, the present invention enables a process for obtaining a pharmaceutical product derived from plant material which comprises the steps of:

(a) obtaining tissue fragments from plant material which is the origin of the pharmaceutical product;

(b) placing said tissue fragments on agar medium until fungal growth occurs;

(c) placing fungal hyphae from said fungal growth on mycological agar until a culture in pure form is obtained;

(d) transferring said fungal hyphae to a fungal lab growth medium, and growing a fungal culture;

(e) removing at least a portion of the culture media containing the fungal culture, thoroughly grinding the mycelium, and adding a chromatographic solvent to the mixture;

(f) obtaining a chromatograph of said fungal culture in said solvent solution; and (g) checking the solution for presence of the pharmaceutical of interest.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. All publications cited herein are incorporated by reference in their entireties. It is to be understood that the phraseology or terminology employed herein is for the purpose of description only and not of limitation.

The following Table 19 shows the production of taxol from various species of fungi in the amounts indicated, the type of tree from which the fungi was isolated and other information.

TABLE 19

| | | FUNGUS COLLECTION | | | | | |
|---|---|---|---|---|---|---|---|
| No. | Culture I.D. Cells | Identification | $MeCl_2$ (mg/L) | Taxol (ng/L) | Pythium Y/N (1x) | Normal Cells(ug) | Cancer |
| | | *TAXUS BACCATA* FROM BRUSSELS | | | | | |
| 1 | Tb(B)-F1 | Mucor | 0 | 0 | n | | |
| 2 | Tb(B)-F2 | | 13.52 | 0 | n | | |
| 3 | Tb(B)-B1 | Muco | — | 0 | n | | |
| 4 | Tb(B)-B2 | pycnidium? | 10.96 | 0 | n | | |
| 5 | Tb(B)-B3 | Phoma | 9.00 | 0 | n | | |
| 6 | Tb(B)-B4 | pycnidium? | 22.56 | 0 | n | | |
| 7 | Tb(B)-B6 | ? | 8.28 | 0 | n | | |
| 8 | Tb(B)-B7 | Cephalosporium | 12.10 | 0 | n | | |
| 9 | Tb(B)-B8 | ? | 12.00 | 0 | n | | |
| 10 | Tb(B)-B9 | ? | | | ++ | | |
| 11 | Tb(B)-P1 | Alternaria | 32.68 | 0 | + | 5.8 | |
| 12 | Tb(B)-P2 | Coryneum(?) | 27.70 | 0 | + | 0.8 | |
| 13 | Tb(B)-X1 | Mucor | — | — | n | | |
| 14 | Tb(B)-X2 | Coniothecium? | 8.10 | 0 | n | | |
| 15 | Tb(B)-X3 | Glomerella | 7.00 | 0 | n | | |
| 16 | Tb(B)-X4 | Phoma | 18.76 | 0 | n | | |
| | | *TAXUS BACCATA* FROM GERMANY | | | | | |
| 17 | Tb(GR)-L1 | Pestalotiopsis | 54.86 | 0 | +++ | 9.9 | |
| 18 | Tb(GR)-2 | Pestalotiopsis | 101.94 | 203.88 | n | ND | |
| 19 | Tb(GR)-3 | Pestalotiopsis | 32.80 | 0 | + | 5.0 | |
| 20 | Tb(GR)-4 | Papularia | 60.63 | 0 | n | ND | |
| 21 | Tb(GR)-L5 | Pestalotiopsis | 203.08 | 398.04 | n | ND | |
| 22 | Tb(GR)-6 | Pestalotiopsis | 115.90 | 834.48 | n | 17.2 | |
| 23 | Tb(GR)-7 | Pestalotiopsis | 112.08 | 430.39 | n | 13.9 | |
| 24 | Tb(GR)-L8 | Pestalotiopsis | 288.26 | 668.76 | n | ND | |
| | | *TAXUS BACCATA* FROM SWITZERLAND | | | | | |
| 25 | Tb(SZ)-1 | Phoma | 10.96 | 0 | +++ | ND | |
| 26 | Tb(SZ)-2 | Sordaria | 9.68 | 0 | n | | |
| 27 | Tb(SZ)-3 | Mucor | 13.38 | 0 | n | | |
| | | *TAXUS BACCATA* FROM MOROCCO | | | | | |
| 28 | Tb(MC)-1 | Fusarium | 178.94 | 0 | ++ | 15.3 | |
| 29 | Tb(MC)-3 | Alternaria | 250.50 | 0 | ++ | 12.0 | |

TABLE 19-continued

FUNGUS COLLECTION

| No. | Culture I.D. Cells | Identification | MeCl$_2$ (mg/L) | Taxol (ng/L) | Pythium Y/N (1×) | Normal Cells(ug) | Cancer |
|---|---|---|---|---|---|---|---|
| 30 | Tb(MC)-4 | Alternaria | 196.64 | 0 | n | | |
| 31 | Tb(MC)-5 | Ulocladium | 25.30 | 0 | n | | |
| 32 | Tb(MC)-6 | Alternaria | 60.86 | 0 | n | | |
| 33 | Tb(MC)-7 | Tricocladium | 30.26 | 0 | n | ND | |
| 34 | Tb(MC)-8 | Mucor | 0 | 0 | n | | |
| 35 | Tb(MC)-10 | Ulocladium | 55.24 | 0 | ++ | 85.7 | |
| 36 | Tb(MC)-i | Alternaria | 32.24 | 0 | n | | |
| | *TORREYA GRANDIFOLIA* FROM HUANGSHAN | | | | | | |
| 37 | T(HS)-L1 | Pestalotiopsis | 158.66 | 761.57 | ++ | ND | |
| 38 | T(HS)-L2 | Nigrospora? | 30.50 | 0 | +++ | ND | |
| 39 | T(HS)-L3 | Pestalotiopsis | 49.34 | 0 | +++ | ND | |
| 40 | T(HS)-L4 | Fusarium | 168.38 | 0 | +++ | 22.6 | |
| 41 | T(HS)-L5 | No spores | 85.18 | 0 | n | ND | |
| 42 | T(HS)-B1 | ? | 11.00 | 0 | | | |
| 43 | T(HS)-B2 | No spores | 15.96 | 0 | | 2.8*0.6 | |
| 44 | T(HS)-B3 | ? | 12.76 | 0 | | | |
| 45 | T(HS)-B4 | No spores | 24.02 | 43.24 | | ND | |
| 46 | T(HS)-B5 | *Humicula Sagenomella?* | 110.30 | 291.19 | | 0.7*0.0 | |
| 47 | T(HS)-B6 | No spores | 31.74 | 71.10 | | 70.6 | |
| 48 | T(HS)-B7 | No spores | 70.92 | 127.66 | | ND | |
| 49 | T(HS)-B8 | No spores | 46.38 | 64.93 | | ND | |
| 50 | T(HS)-B9 | No spores | 83.20 | 316.16 | | ND | |
| 51 | T(HS)-B10 | Acremonium | 37.74 | 0 | | ND | |
| 52 | T(HS)-B11 | | 7.26 | 36.30 | | 40.6 | |
| 53 | T(HS)-X1 | Pestalotiopsis | 83.04 | 0 | ++ | ND | |
| 54 | T(HS)-X2 | Pestalotiopsis | 40.18 | 0 | ++ | ND | |
| 55 | T(HS)-X3 | Pestalotiopsis | 66.92 | 0 | ++ | ND | |
| 56 | T(HS)-X4 | Pestalotiopsis | 30.04 | 0 | +++ | 10.0 | |
| 57 | T(HS)-X5 | Phoma | 17.30 | 0 | n | | |
| 58 | T(HS)-X6 | Pestalotiopsis | 52.20 | 0 | +++ | ND | |
| 59 | T(HS)-X7 | Fusarium (r?) | 181.40 | 0 | +++ | ND | |
| 60 | T(HS)-X8 | Fusarium (o?) | 32.32 | 0 | n | ND | |
| 61 | T(HS)-X10 | No spores | 15.58 | 0 | n | | |
| | *T. CHINENSIS* FROM HUANGSHAN MOUNTAIN | | | | | | |
| 62 | Tc(HSM)-B1 | Cephalosporium? | 18.89 | 0 | +++ | ND | |
| 63 | Tc(HSM)-B2 | Monostichella? | | | +++ | ND | |
| 64 | Tc(HSM)-B3 | No spores | 178.00 | 0 | +++ | 191.0*78.1 | |
| 65 | Tc(HSM)-B4 | Phoma? | 21.40 | 0 | + | | |
| 66 | Tc(HSM)-P1 | Sphaeropsis? | 13.42 | 0 | + | | |
| 67 | Tc(HSM)-P2 | Phoma | 92.18 | 0 | + | ND | |
| 68 | Tc(HSM)-X1 | No spores | 22.74 | 0 | + | ND | |
| 69 | Tc(HSM)-X2 | Phoma | 92.18 | 0 | + | ND | |
| 70 | Tc(HSM)-X3 | Phoma | 16.38 | 0 | ++ | ND | |
| 71 | Tc(HSM)-X4 | No spores | 11.70 | 0 | ++ | ND | |
| 72 | Tc(HSM)-X5 | | 14.04 | 28.08 | n | | |
| | *T. CHINENSIS* FROM HANGZHOU BOTANIC GARDEN | | | | | | |
| 73 | Tc(HSM)-B1 | Pestalotiopsis | 34.68 | 0 | n | ND | |
| 74 | Tc(HSM)-B2 | Pestalotiopsis | 108.14 | 302.79 | | | |
| 75 | Tc(HSM)-B3 | Pestalotiopsis | 40.48 | 40.08 | +++ | ND | |
| 76 | Tc(HSM)-B4 | Cephalosporium? | 14.66 | | +++ | ND | |
| 77 | Tc(HSM)-B5 | Phoma | 26.00 | 0 | +++ | | |
| 78 | Tc(HSM)-B6 | Stagnospora | 15.92 | 0 | n | | |
| 79 | Tc(HSM)-B7 | Phoma | 40.74 | 0 | +++ | ND | |
| 80 | Tc(HSM)-B8 | No spores | 25.12 | 0 | n | | |
| 81 | Tc(HSM)-B9 | No spores | 19.08 | 0 | n | | |
| 82 | Tc(HZG)-P1 | Coniella? | 24.08 | 0 | +++ | 7.2 | |
| 83 | Tc(HZG)-P2 | No spores | 10.70 | 0 | + | | |
| 84 | Tc(HZG)-P3 | No spores | 31.44 | 0 | n | | |
| 85 | Tc(HZG)-P4 | No spores | 13.6 | 0 | n | | |
| 86 | Tc(HZG)-P5 | Stagnospora? | 18.96 | 37.92 | n | | |
| | *CEPHALOTAXUS MAIREI* FROM SHANGHAI BOTANIC GARDEN | | | | | | |
| 87 | Tm(SHG)-B1 | Sphaeropsis | 30.00 | 0 | n | ND | |
| 88 | Tm(SHG)-B2 | Cephalosporium | 25.65 | | +++ | 42.8 | |
| 89 | Tm(SHG)-B3 | Ameriopsis | 19.94 | 0 | ++ | 5.4 | |
| 90 | Tm(SHG)-B4 | Ameriopsis | 23.26 | 0 | ++ | 6.2 | |
| 91 | Tm(SHG)-B5 | Ameeriopsis | 45.90 | | ++ | 0.8 | |
| 92 | Tm(SHG)-B6 | Ameriopsis | 94.38 | | ++ | 0.6 | |
| 93 | Tm(SHG)-B7 | Phoma | 85.46 | 0 | n | 2.7 | |
| 94 | Tm(SHG)-B8 | Microsphaeropsis | 12.32 | 0 | +++ | ND | |

TABLE 19-continued

FUNGUS COLLECTION

| No. | Culture I.D. Cells | Identification | MeCl$_2$ (mg/L) | Taxol (ng/L) | Pythium Y/N (1×) | Normal Cells(ug) | Cancer |
|---|---|---|---|---|---|---|---|
| | *CEPHALOTXUS MAIREI* FROM HANG ZHOU BOTANIC GARDEN | | | | | | |
| 95 | Tm(HZG)-L1 | No spores | 11.20 | 0 | n | | |
| 96 | Tm(HZG)-L2 | Pestalotiopsis | 30.12 | 0 | ++ | ND | |
| 97 | Tm(HZG)-L3 | Pestalotiopsis | 44.56 | 130.12 | ++ | ND | |
| 98 | Tm(HZG)-L4 | Pestalotiopsis | 110.70 | 929.88 | n | ND | |
| 99 | Tm(HZG)-L5 | Pestalotiopsis | 16.10 | 0 | n | ND | |
| 100 | Tm(HZG)-L6 | Pestalotiopsis | 30.90 | 103.82 | n | ND | |
| 101 | Tm(HZG)-L7 | Pestalotiopsis | 25.96 | 46.73 | n | ND | |
| 102 | Tm(HZG)-L8 | Pestalotiopsis | 8.96 | 0 | n | | |
| 103 | Tm(HZG)-L9 | Pestalotiopsis | 18.86 | 0 | + | ND | |
| 104 | Tm(HZG)-B1 | Sphaerosis | 125.74 | 0 | n | ND | |
| 105 | Tm(HZG)-B2 | Pestalotiopsis | 34.20 | 0 | + | ND | |
| 106 | Tm(HZG)-B3 | Amerosporiopsis | 33.50 | 0 | n | 5.9 | |
| 107 | Tm(HZG)-B4 | Phoma | 15.50 | 0 | + | 18.1 | |
| 108 | Tm(HZG)-B5 | Nigrospora | 11.06 | 0 | + | ND | |
| 109 | Tm(HZG)-B6 | Coniella | 12.18 | 0 | n | ND | |
| 110 | Tm(HZG)-B7 | Coniella | | | n | | |
| 111 | Tm(HZG)-B8 | Spheropsis | | | n | ND | |
| 112 | Tm(HZG)-B9 | Pestalotiopsis | 16.20 | 0 | n | ND | |
| 113 | Tm(HZG)-B10 | No spores | 20.30 | 0 | n | | |
| 114 | Tm(HZG)-B11 | No spores | 8.86 | 0 | ++ | ND | |
| 115 | Tm(HZG)-B12 | Hansfordia? | 14.98 | 0 | n | | |
| 116 | Tm(HZG)-B13 | No spores | 163.54 | 0 | n | ND | |
| 117 | Tm(HZG)-B15 | No spores | 27.98 | 0 | +++ | ND | |
| 118 | Tm(HZG)-B16 | | 9.80 | 0 | n | | |
| 119 | Tm(HZG)-X1 | Sphaeropsis | 44.04 | 0 | n | ND | |
| 120 | Tm(HZG)-X2 | Pestalotiopsis | 15.72 | 0 | + | ND | |
| 121 | Tm(HZG)-X3 | Pestalotiopsis | 90.10 | 468.52 | + | ND | |
| 122 | Tm(HZG)-X4 | Pestalotiopsis | 66.90 | 561.96 | +++ | ND | |
| 123 | Tm(HZG)-X5 | Pestalotiopsis | 17.42 | 0 | n | 24.0 | |
| 225 | Tm(HZG)L4-4 | Pestalotiopsis (ss) | 114.0 | 1094.0 | | | |
| 226 | Tm(HZG)L4-11 | Pestalotiopsis (ss) | 118.6 | 105.8 | | | |
| | WESTERN RED CEDAR FROM ROSS CREEK | | | | | | |
| 124 | WRC-B1 | | 65.64 | 85.33 | | | |
| 125 | WRC-B2 | | 10.17 | 6.92 | | | |
| 126 | WRC-B3 | | 21.90 | 14.89 | | | |
| 127 | WRC-B4 | | 22.06 | | | | |
| 128 | WRC-B5 | | 18.99 | 12.15 | | | |
| 129 | WRC-B6 | | 59.40 | 112.86 | | | |
| 130 | WRC-B7 | | 595.46 | 404.9/ | | | |
| 131 | WRC-B8 | Alternaria | 553.34 | 376.27 | | | |
| 132 | WRC-B9 | | 50.58 | 80.93 | | | |
| 133 | WRC-B10 | | 9.45 | 3.24 | | | |
| 134 | WRC-B11 | | 4.31 | | | | |
| 135 | WRC-B12 | | 9.72 | 8.39 | | | |
| 136 | WRC-B13 | | 13.99 | 6.65 | | | |
| 137 | WRC-B14 | Cephalosporium/ Acremonium | 13.85 | | | | |
| 138 | WRC-B15 | | 7.50 | | | | |
| 139 | WRC-B16 | | 8.14 | | | | |
| 140 | WRC-B17 | | 6.07 | | | | |
| 141 | WRC-P1 | | 9.36 | | | | |
| 142 | WRC-P2 | | 10.46 | | | | |
| 143 | WRC-P3 | | 8.08 | | | | |
| | *TAXUS BREVIFOLIA* FROM ROSS CREEK | | | | | | |
| 144 | Tb(RC)B-1 | Trichoderma | 107.60 | 64.56 | | | |
| 145 | Tb(RC)B-2 | Trichoderma | 91.18 | 65.65 | | | |
| 146 | Tb(RC)B-3 | | 72.91 | | | | |
| 147 | Tb(RC)B-4 | no spores | 13.12 | 5.77 | | | |
| 148 | Tb(RC)B-5 | | 75.45 | | | | |
| 149 | Tb(RC)B-6 | Trichosporiella? | 14.74 | 10.61 | | | |
| 150 | Tb(RC)B-7 | Ulocladium | 22.39 | | | | |
| 151 | Tb(RC)B-8 | no spores | 78.08 | 34.36 | | | |
| 152 | Tb(RC)B-9 | Pennicillium | 74.09 | | | | |
| 153 | Tb(RC)B-10 | Cephalosporium/ Acremonium | 11.38 | | | | |
| 154 | Tb(RC)B-11 | Epicoccum | 398.37 | | | | |
| 155 | Tb(RC)B-12 | Ulocladium | 23.40 | | | | |
| 156 | Tb(RC)B-13 | Cephalosporium/ Acremonium | 53.99 | | | | |

TABLE 19-continued

FUNGUS COLLECTION

| No. | Culture I.D. Cells | Identification | MeCl$_2$ (mg/L) | Taxol (ng/L) | Pythium Y/N (1×) | Normal Cells(ug) | Cancer |
|---|---|---|---|---|---|---|---|
| 157 | Tb(RC)B-14 | | 95.29 | | | | |
| 158 | Tb(RC)B-15 | Cephalosporium/ Acremonium | 24.28 | | | | |
| 159 | Tb(RC)B-16 | Cephalosporium/ Acremonium | 23.74 | | | | |
| 160 | Tb(RC)B-17 | Cephalosporium/ Acremonium | 6.07 | | | | |
| | | *TAXUS BACCATA* | | | | | |
| 161 | TbP1 | Alternaria | | | | | |
| 162 | TbP2 | Monochaeta | 58.7 | 102.7 | | | |
| 163 | TbP3 | Phoma | 11.7 | 0 | | | |
| 164 | TbP4 | Monochaeta | | | | | |
| 165 | TbP5 | Cephalosporium/ Acremonium | 17.6 | 11.3 | | | |
| 166 | TbP6 | | | | | | |
| 167 | TbP7 | | | | | | |
| 168 | TbP8 | | | | | | |
| 169 | TbP9 | Fusarium | 94.7 | 130.7 | | | |
| 170 | TbP10 | Melanconium? | 94.1 | 0 | | | |
| 171 | TbP11 | Pestalotiopsis | | | | | |
| 172 | TbP12 | Pestalotiopsis | | | | | |
| 173 | TbP13 | Melanconium? | | | | | |
| 174 | TbP14 | | 61.7 | 129.6 | | | |
| 175 | TbP15 | | | | | | |
| 176 | TbP16 | | | | | | |
| 177 | TbP17 | | | | | | |
| 178 | TbX1 | Pestalotiopsis | | | | | |
| 179 | TbX2 | Pestalotiopsis | 587.5 | 1081.0 | | | |
| 180 | TbX3 | Coniothyrium? | | | | | |
| 181 | TbX4 | | 68.0 | 49.0 | | | |
| 182 | TbX5 | | | | | | |
| 183 | TbX6 | Coniothyrium? | 54.3 | 380.1 | | | |
| | | *TORREYA TAXIFOLIA* | | | | | |
| 184 | TtB1 | Pestalotiopsis | 27.8 | 0 | | | |
| 185 | TtB2 | Trichoderma | 9.5 | 23.75 | | | |
| 186 | TtB3 | Curvularia | 126.2 | 323.07 | | | |
| 187 | TtB4 | Pestalotiopsis | 32.0 | 41.92 | | | |
| 188 | TtB5 | Penicillium | 108.9 | 213.44 | | | |
| 189 | TtP1 | NI(pycnidia) | 21.6 | 19.01 | | | |
| 190 | TtP2 | | 21.6 | 19.01 | | | |
| 191 | TtX1 | Pestalotiopsis | 87.1 | ? | | | |
| 192 | TtX3 | | 13.1 | 0 | | | |
| | | CYPRESS | | | | | |
| 193 | CB1 | | 50.5 | 242.4 | | | |
| 194 | CB2 | Pestalotiopsis | 17.0 | 59.5 | | | |
| 195 | CB3 | Pestalotiopsis | 7.6 | 54.7 | | | |
| 196 | CB4 | Pestalotiopsis | 35.4 | 99.1 | | | |
| 197 | CB5 | Pestalotiopsis | 13.0 | | | | |
| 198 | CB8 | Pestalotiopsis | 10.1 | | | | |
| 199 | CB9 | Pestalotiopsis | 9.1 | | | | |
| 200 | CP1 | Pestalotiopsis | 13.7 | 24.7 | | | |
| 201 | CP2 | Pestalotiopsis | 36.5 | 116.8 | | | |
| 202 | CP3 | (pycnidia) | 12.3 | 14.8 | | | |
| 203 | CP4 | Pestalotiopsis | 69.2 | 1487.8 | | | |
| 204 | CP5 | (pycnidia) | 16.5 | | | | |
| 205 | CP6 | Pestalotiopsis | 12.9 | 82.6 | | | |
| 206 | CP7 | Pestalotiopsis | 11.9 | | | | |
| 207 | CP8 | Pestalotiopsis | 28.0 | | | | |
| 208 | CP9 | Pestalotiopsis | 13.2 | | | | |
| 209 | CP10 | Pestalotiopsis | 16.5 | 85.7 | | | |
| 210 | CX1 | Pestalotiopsis | 10.8 | 14.2 | | | |
| 211 | CX2 | Pestalotiopsis | 54.2 | 498.4 | | | |
| 212 | CX3 | Pestalotiopsis | 16.9 | | | | |
| 213 | CX4 | Pestalotiopsis | 30.9 | | | | |
| | | WOLLEMI PINE FROM AUSTRALIA | | | | | |
| 214 | WL1 | Pestalotiopsis | 100.0 | 172.0 | | | |
| 215 | WL2 | *P. guelpii* | 195.9 | 485.7 | | | |
| 216 | WL6 | Pestalotiopsis | 64.8 | | | | |
| 217 | WB1 | | | | | | |
| 218 | WB2 | | | | | | |

TABLE 19-continued

FUNGUS COLLECTION

| No. | Culture I.D. Cells | Identification | MeCl$_2$ (mg/L) | Taxol (ng/L) | Pythium Y/N (1x) | Normal Cells(ug) | Cancer |
|---|---|---|---|---|---|---|---|
| 219 | WB3 | | 41.5 | | | | |
| 220 | WB5 | | | | | | |
| 221 | WB6 | | 21.9 | | | | |
| 222 | WB7 | | 10.8 | | | | |
| 223 | WB9 | | 15.5 | | | | |
| 224 | WB14 | Xylaria? | 47.0 | | | | |
| 225 | WP2 | Penicillium | 133.8 | | | | |
| 226 | WX1H1 (Hyg R) | Pestalotiopsis | | | | | |
| 227 | WX1 | Pestalotiopsis | 64.6 | | | | |
| 228 | WX3 | Pestalotiopsis | 98.96 | 127.7 | | | |
| | | *TSUGA CANADENSIS* from Monticello, VA | | | | | |
| 548 | Ch(M, V)B-3 | Sclerostagnospora or Stagnospora | 23.42 | 14.99 | | 44.6 | |
| 547 | Ch(M, V)B-2 | Basidiomycete | 10.84 | 16.04 | — | | 12.2 |
| 546 | Ch(M, V)B-1 | No spores 35.6 | 37.02 | — | | 1.0 | |
| | | CORYLUS SP (FILBERT FROM OREGON) | | | | | |
| | BF1 | | 81.6 | 0 | | | |
| | FIB3 | | 58.2 | 0 | | | |
| | FIB11 | | 18.7 | 0 | | | |
| | BF2 | Botrytis | 188.25 | 406.6 | | | |
| | FIB8 | A Basidiomycete | 24.8 | 29.8 | | | |
| | FC2 | Phoma | 15.9 | 17.8 | | | |
| | FC3 | A Yeast | 54.8 | 81.1 | | | |
| | FIB10 | | 17.5 | ? | | | |

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. All publications cited herein are incorporated by reference in their entireties. It is to be understood that the phraseology or terminology employed herein is for the purpose of description only and not of limitation.

What is claimed is:

1. A biologically pure culture of a microbe which produces taxol or taxane in culture, wherein the fungus is Taxomyces.

2. A biologically pure culture of a microbe which produces taxol or taxane in culture, wherein the microbe is obtained from a tree.

3. A biologically pure culture according to claim 2, wherein the tree is selected from the group consisting of Yew tree, *Torreya Grandifolia, Tsuga Canadersis,* Covylus (Filbert), Bristle Cove Pine, White Bark Pine, *Torreya Taxifolia,* Canadian Hemlock, Western Red Cedar, Cypress, Cephalotaxus and Wollemi Pine.

4. A biologically pure culture of a fungus which produces taxol isolated from a tree.

5. A fungus according to claim 4, wherein said fungus is an endophytic fungus.

6. A fungus according to claim 5, wherein said fungus is of the taxonomic family *Fungi imperfecti.*

7. A fungus according to claim 5, wherein said fungus is of the taxonomic family Hyphomyces.

8. A fungus according to claim 7, wherein said fungus is of the taxonomic genus Taxomyces.

\* \* \* \* \*